(12) United States Patent
Sullivan et al.

(10) Patent No.: US 12,245,949 B2
(45) Date of Patent: Mar. 11, 2025

(54) INTERLAMINAR LUMBAR INTERBODY FUSION SYSTEM AND ASSOCIATED ROBOTIC SYSTEMS

(71) Applicant: GLOBUS MEDICAL, INC., Audubon, PA (US)

(72) Inventors: Myles Sullivan, Philadelphia, PA (US); Mark Weiman, Downingtown, PA (US); Carly Taubenkraut, Perkasie, PA (US); Chad Glerum, Pennsburg, PA (US)

(73) Assignee: Globus Medical Inc., Audubon, PA (US)

( * ) Notice: Subject to any disclaimer, the term of this patent is extended or adjusted under 35 U.S.C. 154(b) by 792 days.

(21) Appl. No.: 17/381,406

(22) Filed: Jul. 21, 2021

(65) Prior Publication Data
US 2023/0028545 A1 Jan. 26, 2023

Related U.S. Application Data

(63) Continuation of application No. 17/380,267, filed on Jul. 20, 2021.

(51) Int. Cl.
| | | |
|---|---|---|
| *A61F 2/44* | (2006.01) |
| *A61B 17/70* | (2006.01) |
| *A61B 17/92* | (2006.01) |
| *A61B 34/20* | (2016.01) |
| *A61B 34/30* | (2016.01) |

(Continued)

(52) U.S. Cl.
CPC ........ *A61F 2/4455* (2013.01); *A61B 17/7013* (2013.01); *A61B 17/92* (2013.01); *A61B 34/20* (2016.02); *A61B 34/30* (2016.02); *A61B 90/39* (2016.02); *A61F 2/442* (2013.01); *A61F 2/4611* (2013.01); *A61B 2017/00876* (2013.01); *A61B 2017/922* (2013.01); *A61B 2034/2046* (2016.02); *A61B 2034/301* (2016.02); *A61B 2090/3983* (2016.02); *A61F 2002/4632* (2013.01)

(58) Field of Classification Search
CPC .................. A61F 2/4455; A61F 2/4611; A61F 2002/448–4485
See application file for complete search history.

(56) References Cited

U.S. PATENT DOCUMENTS

| | | |
|---|---|---|
| 6,607,530 B1 | 8/2003 | Carl et al. |
| 6,923,811 B1 | 8/2005 | Carl et al. |

(Continued)

FOREIGN PATENT DOCUMENTS

| | | |
|---|---|---|
| EP | 3241518 A3 | 1/2018 |
| EP | 3510927 A1 | 7/2019 |

(Continued)

*Primary Examiner* — Eduardo C Robert
*Assistant Examiner* — Michelle C Green

(57) ABSTRACT

Orthopedic implants, systems, instruments, and methods. A bi-portal lumbar interbody fusion system may include an expandable interbody implant and minimally invasive pedicle-based intradiscal fixation implants. The interbody and intradiscal implants may be installed with intelligent instrumentation capable of repeatably providing precision placement of the implants. The bi-portal system may be robotically-enabled to guide the instruments and implants along desired access trajectories to the surgical area.

13 Claims, 40 Drawing Sheets

(51) Int. Cl.
*A61B 90/00* (2016.01)
*A61F 2/46* (2006.01)
*A61B 17/00* (2006.01)

(56) References Cited

U.S. PATENT DOCUMENTS

| | | |
|---|---|---|
| 7,497,868 B2 | 3/2009 | Steinberg |
| 8,021,401 B2 | 9/2011 | Carl et al. |
| 8,221,460 B2 | 7/2012 | Mathews |
| 8,747,476 B2 | 6/2014 | Steinberg |
| 9,017,313 B2 | 4/2015 | Steinberg |
| 9,198,678 B2 | 12/2015 | Frey et al. |
| 9,398,962 B2 | 7/2016 | Steinberg |
| 9,561,115 B2 | 2/2017 | Elahinia et al. |
| 9,788,966 B2 | 10/2017 | Steinberg |
| 9,827,109 B2 | 11/2017 | Steinberg |
| 9,949,800 B2 | 4/2018 | Prisco et al. |
| 10,285,821 B2 | 5/2019 | Schaller et al. |
| 10,485,675 B2 * | 11/2019 | Sharifi-Mehr .......... A61F 2/442 |
| 10,695,133 B2 | 6/2020 | Stanton et al. |
| 10,751,127 B2 | 8/2020 | Dace et al. |
| 10,786,264 B2 | 9/2020 | Chegini et al. |
| 11,219,535 B1 * | 1/2022 | Hauck ................... A61F 2/4611 |
| 2008/0033432 A1 * | 2/2008 | McGraw ............ A61B 17/7098 606/86 A |
| 2009/0005816 A1 * | 1/2009 | Denardo ............ A61B 17/1631 606/100 |
| 2010/0016903 A1 * | 1/2010 | Matityahu ............ A61B 17/866 606/301 |
| 2010/0094346 A1 * | 4/2010 | Matityahu .......... A61B 17/7041 606/264 |
| 2010/0305700 A1 * | 12/2010 | Ben-Arye ............. A61B 17/70 606/279 |
| 2015/0257894 A1 * | 9/2015 | Levy ....................... A61F 2/442 623/17.15 |
| 2017/0360480 A1 * | 12/2017 | Sekhon .............. A61B 17/8635 |
| 2020/0030013 A1 * | 1/2020 | Gonzalez Blohm ... A61B 17/70 |
| 2020/0375436 A1 | 12/2020 | Kielack et al. |
| 2021/0068863 A1 | 3/2021 | Choi et al. |
| 2021/0113238 A1 | 4/2021 | Donovan |
| 2021/0186709 A1 * | 6/2021 | Weiman ................ A61F 2/4425 |

FOREIGN PATENT DOCUMENTS

| | | |
|---|---|---|
| JP | 2016524506 A | 8/2016 |
| JP | 2017205495 A | 11/2017 |
| WO | 2012092329 A1 | 7/2012 |
| WO | 2013048951 A1 | 4/2013 |
| WO | 2018227180 A1 | 12/2018 |

\* cited by examiner

INTERLAMINAR LUMBAR INTERBODY FUSION SYSTEM AND ASSOCIATED ROBOTIC SYSTEMS

CROSS REFERENCE TO RELATED APPLICATIONS

The present application is a continuation application of U.S. patent application Ser. No. 17/380,267 filed on Jul. 20, 2021, which is incorporated in its entirety herein.

FIELD OF THE INVENTION

The present application relates generally to orthopedic fixation devices, such as lumbar interbody fusion implants, intradiscal implants, associated instruments, and associated methods, for example, for spine surgery.

BACKGROUND OF THE INVENTION

Transforaminal lumbar interbody fusion (TLIF) procedures are a standard surgery technique to provide support and stabilize the spinal vertebra and the disc space when treating a variety of spinal conditions, such as degenerative disc disease and spinal stenosis with spondylolisthesis. Clinical treatment of spinal pathologies may include precise placement of an interbody to restore anterior column alignment with bilateral pedicle screw (BPS) fixation to stabilize two or more adjacent vertebral bodies adjacent to spinal fusion levels.

Various iatrogenic pathologies may occur in association with interbody and bilateral pedicle screw placement. These pathologies may result from the surgical access window to the disc space, failure to precisely place the interbody along the apophyseal ring for quality cortical bone support, and/or failure to restore normal anatomical spinal alignment. Iatrogenic pathologies associated with pedicle screw fixation, may include, but are not limited to, misplacement of screws, muscle/ligament disruption during insertion, adjacent segment disease due to superior adjacent facet violation by the pedicle screw, and rod construct, procedural efficiency, and instrumentation failure.

The instrumentation needed to provide access into the disc through a tubular approach, provide a valued decompression, complete a quality discectomy efficiently, insert and deploy an interbody, and insert the pedicle screw and rod construct also require a multitude of radiographic imaging throughout the procedure. This all increases surgical operating time, radiation exposure, and can result in the misplacement of implants and screws.

There exists a clinical need for a robotically enabled procedure that provides pre-operative planning that is compatible with navigated, intelligent instrumentation that (1) establishes safe and repeatable direct decompression while gaining access to the disc space; (2) provides enhanced navigated, powered discectomy technique; (3) allows for precision placement of an expandable interbody that increases surface area contact along the apophyseal ring through the posterior approach; and/or (4) utilizes a minimally invasive fixation method that stabilizes the adjacent vertebral bodies without violating the superior facet.

SUMMARY OF THE INVENTION

To meet this and other needs, orthopedic implants, systems, instruments, and methods are provided. The implant system may include a three-legged expandable interbody used alone or in combination with one or more pedicle-based intradiscal fixation implants. The implants may be installed using a robotically-enabled bi-portal lumbar interbody fusion procedure with intelligent instrumentation capable of repeatably providing clinically superior segmental correction through stabilization and fixation methods that avoid violation of the superior adjacent facet joint for patients with one- or two-level degenerative conditions. The procedure may include one or more aspects of the following workflow which may be assisted and enhanced using imaging, navigation and/or robotics: (1) pre-operative planning; (2) end-effector set-up; (3) tubular access and decompression or alternative visualization port workflows; (4) bi-portal implant cannula insertion; (5) bi-portal discectomy; (6) interbody deployment, positioning, and expansion; (7) nitinol fixation construction; and (8) final verification.

According to one embodiment, an orthopedic system for stabilizing the spine includes an expandable interbody implant and first and second pedicle-based intradiscal implants. The expandable interbody implant may include a first expandable lateral leg, a second expandable lateral leg, and a third central leg pivotably connected between the first and second lateral legs. The first and second lateral legs are independently expandable in height to provide lordotic and/or coronal adjustments. The first and second pedicle-based intradiscal implants may each include a nitinol rod and a pedicle screw securable to the nitinol rod.

The pedicle-based intradiscal implant may include one or more of the following features. The nitinol rod may extend from a proximal end configured to mate with the pedicle screw to a distal end configured to engage bone. The nitinol rod may have a naturally curved state and the nitinol rod may be straightened for deployment. The curved state of the nitinol rod may be an arc up to 180°. The nitinol rod may have a polygonal cross-section with planar faces. The nitinol rod may be configured to be inserted through a pedicle of an inferior vertebra, through a vertebral body of the inferior vertebra, through a disc space, and into a vertebral body of a superior vertebra. The proximal end of the nitinol rod may include an externally threaded portion configured to mate with an internally threaded portion of the pedicle screw. The pedicle screw may include a screw head with a threaded or roughened texture configured to be engaged by a polyaxial tulip head.

The expandable interbody implant may include one or more of the following features. The first and second lateral legs of the expandable interbody implant may be configured to angulate at one or more pins to increase the overall footprint of the implant. The first and second lateral legs may each include an actuation assembly including a drive screw configured to expand the first and second lateral legs and the central leg of the expandable interbody implant.

According to one embodiment, a pedicle-based intradiscal implant includes a bendable rod and a pedicle screw. The bendable rod may be comprised of a shape-memory material, such as nitinol. The bendable rod may extend from a proximal end having an outer threaded portion to a distal end with a sharp tip configured to engage bone. The bendable rod may have a polygonal cross-section with planar faces. The pedicle screw may extend from a proximal end with a screw head to a distal end with a tip configured to engage the bendable rod. The pedicle screw may have a threaded shaft with a hollow body for receiving the proximal end of the bendable rod. The threaded shaft may define an internal threaded portion configured to mate with the outer threaded portion of the bendable rod.

According to another embodiment, a system for deploying the pedicle-based intradiscal implant includes a deployment instrument configured to load and deploy the bendable rod. The deployment instrument includes a body having a longitudinal axis with a straight deployment tube configured to draw in the curved rod, thereby straightening the rod when held within the deployment tube, and a shaft with an impaction cap. The deployment instrument may include a T-shaped handle with a socket configured to be received over the shaft with the impaction cap. When the handle is rotated about the longitudinal axis of the deployment instrument, the bendable rod is drawn into the deployment tube. When the shaft of the deployment instrument is translated distally along the longitudinal axis of the instrument by striking the impaction cap, the shaft forces the bendable rod to deploy out of the deployment tube.

According to another embodiment, a method for stabilizing the spine includes (1) positioning an expandable interbody implant in a disc space between superior and inferior vertebrae, the expandable interbody implant having three articulating and expandable legs; (2) deploying a first bendable rod from an ipsilateral pedicle of the inferior vertebra, thru the disc space, and into a vertebral body of the superior vertebra; (3) inserting a first pedicle screw through the ipsilateral pedicle of the inferior vertebra and driving the first pedicle screw over the first bendable rod to anchor the first bendable rod; (4) deploying a second bendable rod from a contralateral pedicle of the inferior pedicle, thru the disc space, and into the vertebral body of the superior vertebra; and (5) inserting a second pedicle screw through the contralateral pedicle of the inferior pedicle and driving the second pedicle screw over the second bendable rod to anchor the second bendable rod.

The method may further include articulating the three legs of the expandable interbody implant relative to one another to increase the overall footprint of the implant. The expandable interbody implant may be placed along the apophyseal ring of the vertebrae for cortical bone support. The expandable interbody implant may be expanded to independently control sagittal and coronal correction. The expandable interbody implant may be positioned in the disc space by inserting a magnetic cable assembly attached to the expandable interbody implant through an ipsilateral cannula, inserting an articulating magnet retrieval tool through a contralateral cannula to magnetically attract and connect to the magnetic cable assembly, and retracting the articulating magnet retrieval tool back through the contralateral cannula, thereby pulling the cable assembly into the contralateral cannula and positioning the expandable interbody implant in the disc space. The first intradiscal implant may be deployed through an ipsilateral cannula and the second intradiscal implant may be deployed through a contralateral cannula. The first and second intradiscal implants may be positioned medially relative to the expandable interbody implant. The first and second bendable rods may each be deployed with a deployment instrument having a deployment tube and a shaft with an impaction cap. Each bendable rod may be deployed by striking the impaction cap, thereby forcing the rod to deploy out of the deployment tube.

According to another embodiment, a method of installing an expandable interbody implant in a disc space between two adjacent vertebrae may include: (1) inserting a cable assembly through an ipsilateral cannula, the cable assembly including a cable with a magnetic tip at one end and attachable to an expandable interbody implant at the other end, the expandable interbody implant having a first expandable lateral leg, a second expandable lateral leg, and a third central leg pivotably connected between the first and second lateral legs; (2) inserting an articulating magnet retrieval tool through a contralateral cannula; (3) articulating and guiding the articulating magnet retrieval tool toward the ipsilateral cannula to magnetically attract and connect to the magnetic tip of the cable assembly; and (4) retracting the articulating magnet retrieval tool back through the contralateral cannula, thereby pulling the cable assembly into the contralateral cannula and positioning the expandable interbody implant in the disc space.

The method of installing the expandable interbody implant may further include threading the cable assembly on the first expandable lateral leg of the expandable interbody implant before inserting the cable assembly through the ipsilateral cannula. The method may include attaching a first inserter to the expandable interbody implant while placing the cable under tension. The method may include feeding the expandable interbody implant through the ipsilateral cannula with the first inserter while the cable assembly pulls the expandable interbody implant into an articulated U-shaped position. After removing the cable assembly from the expandable interbody implant, a second inserter may be attached to the expandable interbody implant such that the first and second inserters are rigidly connected to the first and second lateral legs, respectively, thereby providing for dual control of the expandable interbody implant. The method may also include inserting a driver through each of the first and second inserters to independently expand the first and second lateral legs to control sagittal and coronal correction.

According to yet another embodiment, a method for installing a pedicle-based intradiscal implant may include (1) loading a deployment instrument including a body having a longitudinal axis with a straight deployment tube and a shaft with an impaction cap, by drawing a rod having a naturally curved shape into the straight deployment tube, thereby straightening the rod when held within the deployment tube; (2) positioning the deployment tube at a pedicle of an inferior vertebra; and (3) deploying the rod from the deployment instrument by striking the impaction cap to translate the shaft of the deployment instrument along the longitudinal axis, thereby forcing the rod to deploy out of the deployment tube, wherein once deployed, the rod extends from the pedicle, thru a disc space, and into a vertebral body of a superior vertebra. The method for installing the pedicle-based intradiscal implant may further include securing a pedicle screw through the pedicle of the inferior vertebra and driving the pedicle screw over one end of the rod to anchor the rod.

According to another embodiment, a bi-portal robotically-enabled system may include a robotic system and a bi-portal assembly. The robotic system may include a base, including a computer, a display electronically coupled to the computer, a robot arm electronically coupled to the computer and movable based on commands processed by the computer, an end-effector having a guide tube electronically coupled to the robot arm, the guide tube having a central longitudinal axis, and a camera configured to detect one or more tracking markers. The bi-portal assembly may include a guide bar assembly supporting first and second navigated cannula assemblies. The guide bar assembly may include a central guide bar configured to be inserted into the guide tube and first and second lateral wings positioned on opposite sides of the guide bar. The first and second navigated cannula assemblies may each include a hollow tubular cannula configured to guide an instrument placed through the respective cannula along a desired access trajectory to a surgical area.

The bi-portal robotically-enabled system may include one or more of the following features. The bi-portal assembly may be configured to pivot about the central longitudinal axis of the guide tube of the end-effector. The first and second navigated cannula assemblies may each be configured to independently angulate with respect to the central longitudinal axis of the guide tube, thereby providing the desired access trajectories to the surgical area. The width between the cannulas of the first and second navigated cannula assemblies may be adjustable. The bi-portal assembly may include a plurality of tracking markers configured to monitor the guide bar assembly and first and second navigated cannula assemblies, thereby providing navigated and/or robotic assistance. The first lateral wing may support the first navigated cannula via a first supporting arm and the second lateral wing may support the second navigated cannula via a second supporting arm. The first and second lateral wings may each include an elongate slot, and the navigated cannula assemblies may slide along the respective slots to adjust the width and/or angulation of the cannulas. The guide bar may be configured to slide into and lock axially to the guide tube of the end-effector with an axial locking cap. The axial locking cap may include a locking button configured to engage with a groove on the guide bar. Rotational movement of the guide bar assembly may be lockable with a central wheel handle lock.

According to another embodiment, a bi-portal assembly may include a guide bar assembly and first and second navigated cannula assemblies. The guide bar assembly may include a central guide bar configured to be inserted into a guide tube of a robot system and first and second lateral wings positioned on opposite sides of the guide bar. The first and second lateral wings may each including an elongate slot. The first navigated cannula assembly may include a first cannula coupled to the first lateral wing. The first cannula may be configured to guide an instrument placed through the first cannula along a first access trajectory. The second navigated cannula assembly may include a second cannula coupled to the second lateral wing. The second cannula may be configured to guide an instrument placed through the second cannula along a second access trajectory. The first and second navigated cannula assemblies may slide along the respective slots in the first and second lateral wings to adjust the width and/or angulation of the first and second cannulas.

The bi-portal assembly may include one or more of the following features. The first and second navigated cannula assemblies may move along one or more ratchets, thereby providing for incremental adjustment of the width and/or angle of the first and second cannulas. The ratchets may include curvilinear ratchets configured to mimic the shape of the first and second lateral wings. The ratchets may be positioned above and below each of the elongate slots. The first and second navigated cannula assemblies may each include a rotatable knob configured to independently lock a final position of the first and second cannulas. The bi-portal assembly may include a plurality of tracking markers on the guide bar, the first and second lateral wings, and the first and second cannulas.

According to yet another embodiment, a bi-portal robotically-enabled method may include: (1) performing pre-operative planning with a robotic system having an end-effector with a guide tube including taking pre-operative images and planning positioning of one or more implants; (2) introducing a guide bar of a bi-portal assembly into the guide tube of the end-effector, the bi-portal assembly comprising a guide bar assembly supporting first and second navigated cannula assemblies each configured to guide an instrument along a desired access trajectory; (3) accessing a surgical site through the first and second navigated cannula assemblies to perform a decompression; (4) positioning implant cannulas through the first and second navigated cannula assemblies; (5) performing a discectomy through the implant cannulas; (6) deploying an interbody implant through the implant cannulas; (7) installing intradiscal implants through the guide tube of the end-effector; and (8) verifying final positioning of the interbody and intradiscal implants. The first and second navigated cannula assemblies may each include an adjustable depth stop configured to set the access depth into the surgical site.

Also provided are kits including implants of varying types and sizes, rods, fasteners or anchors, various instruments and tools, k-wires, and other components for performing the procedures.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Embodiments of the disclosure are generally directed to orthopedic implants, systems, instruments, and methods. In particular, a bi-portal lumbar interbody fusion procedure may include an expandable interbody that increases surface area contact along the apophyseal ring through the posterior approach and minimally invasive pedicle-based intradiscal fixation implants that stabilize the adjacent vertebral bodies without violating the superior facet. The interbody and intradiscal implants may be installed with intelligent instrumentation capable of repeatably providing precision placement of the implants. The procedure may be performed with or without navigation and/or robotic assistance. The robotically-enabled procedure may utilize imaging, navigation, and robotics to enhance the quality and efficiency of the posterior procedure through planning and navigable instrumentation.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments and modifications thereof are contemplated as falling within the scope of this disclosure and equivalents thereto.

Figure 1A:
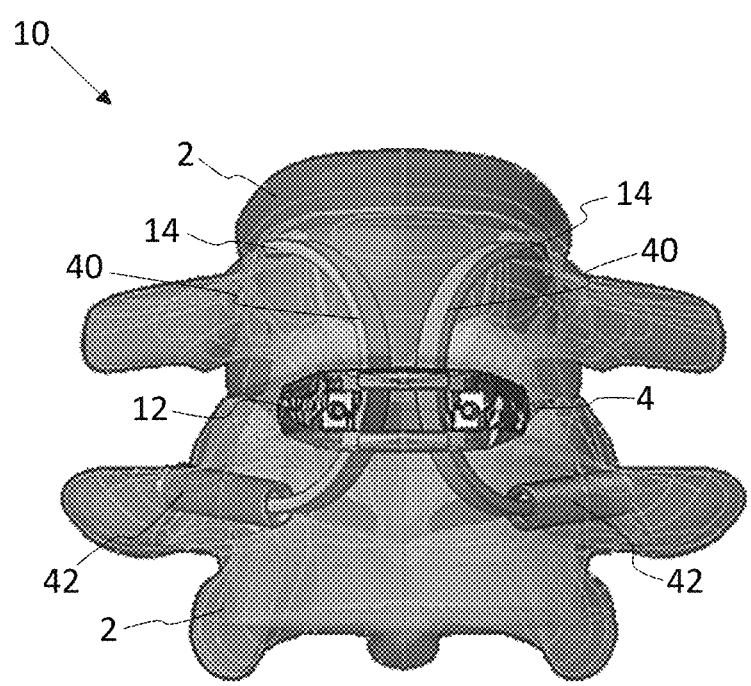
FIGS. 1A-1C shows anterior, lateral, and axial views, respectively, of adjacent vertebrae with a fixation system including a three-legged expandable interbody and a pair of pedicle-based intradiscal fixation implants according to one embodiment.
Figure 1B:
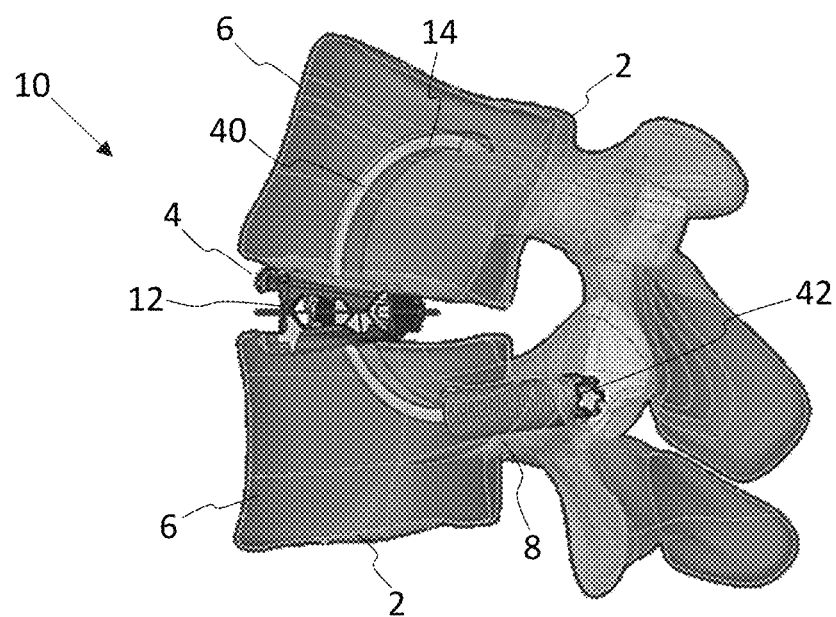
Figure 1C:
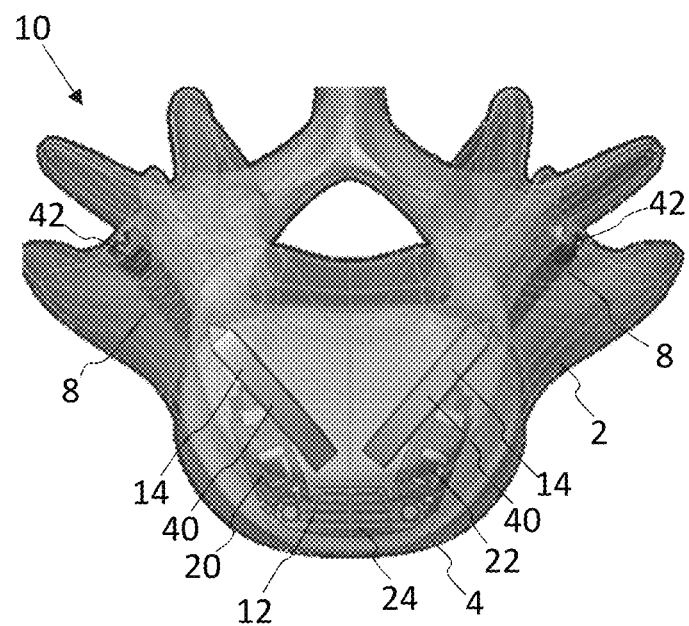
Figure 2A:
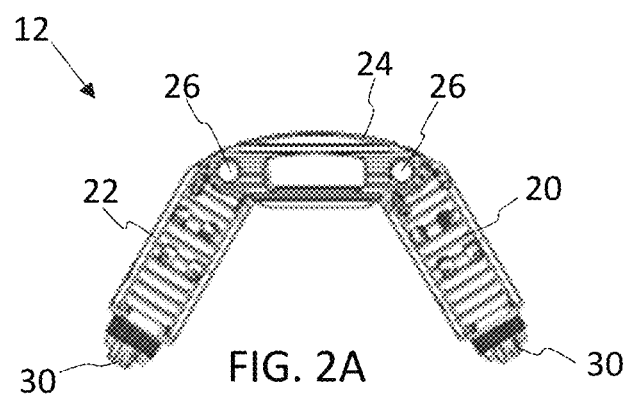
FIGS. 2A-2D show top, rear, and side views, respectively, of a three-legged expandable interbody implant according to one embodiment.
Figures 2B, 2C, 2D:
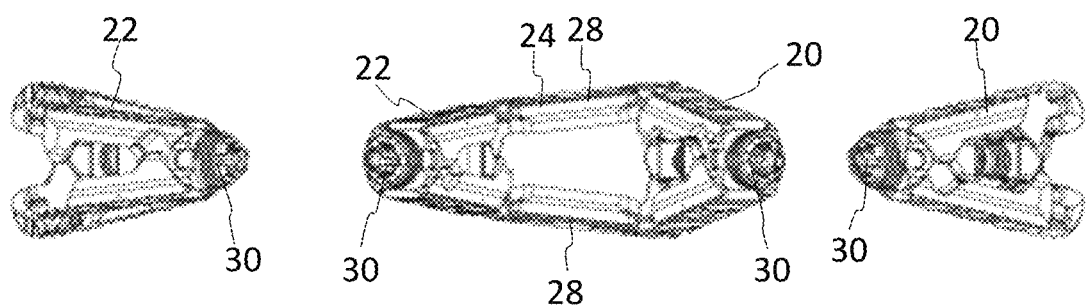

Referring now to FIGS. 1A-1C, an interlaminar lumbar interbody fusion system or orthopedic fixation system 10 is shown for fusing two adjacent vertebrae 2. The fixation system 10 may include an expandable interbody implant 12 and one or more pedicle-based fixation implants 14. The expandable interbody implant 12 is positioned in the disc space 4 between the superior and inferior vertebral bodies 6. The interbody implant 12 may be placed along the apophyseal ring for cortical bone support. The expandable interbody implant 12 may include dual, independent expansion and angulation to adjust lordosis and/or coronal balance, thereby allowing for restoration of spinal anatomical alignment. The pedicle fixation implant 14 may include an intradiscal device configured to be deployed from the inferior pedicle 8, thru inferior vertebral body 6, thru the intradiscal space 4, and into the superior vertebral body 6. First and second pedicle fixation implants 14 may be positioned through the pedicles 8 of the inferior vertebra 2 and medially relative to the interbody implant 12. The fixation system 10 may provide for superior segmental correction from stabilization device 12 with independently controlled sagittal and coronal correction and increased stability from increased endplate contact along the apophyseal ring as well as a fixation construct that avoids violation of the superior facet joint and the potential iatrogenic effects of a traditional bilateral pedicle construct.

Turning now to FIGS. 2A-2D, the expandable interbody implant 12 may include three sections or legs 20, 22, 24, which are configured to articulate or pivot relative to one another at pins 26 to increase the overall width or footprint of the implant 12. The implant 12 may include a first expandable lateral leg 20, a second expandable lateral leg 22, and a third anterior leg or central leg 24 with link plates 28, which connect the first and second lateral legs 20, 22. Each of the lateral leg 20, 22 may include an actuation assembly 30, for example, including a drive screw or actuator configured to move a plurality of driving ramps, which expand the endplates of the lateral legs 20, 22 in height. When the first and/or second lateral legs 20, 22 are independently expanded in height, the attached link plates 28 are configured to passively increase in height, thereby providing lordotic and/or coronal adjustments.

Figure 3:
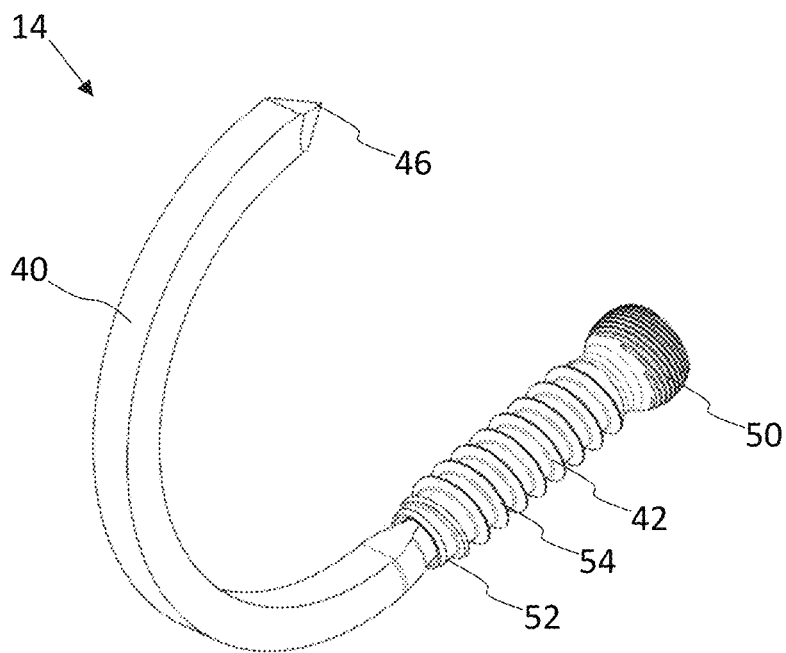
FIG. 3 shows a perspective view of a pedicle-based intradiscal fixation implant according to one embodiment.
Figure 4A:
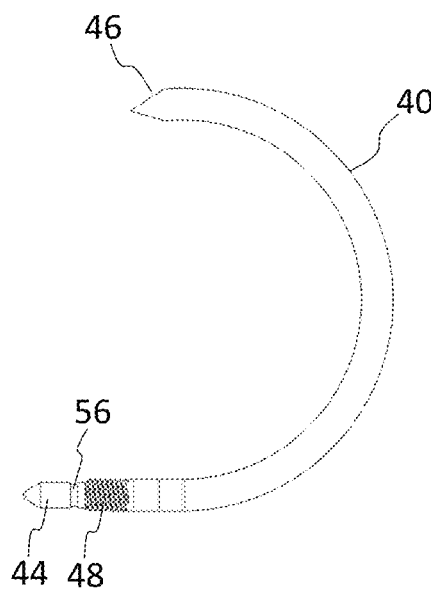
FIGS. 4A-4B shows the components of the pedicle-based intradiscal fixation implant of FIG. 3 including the nitinol rod and a pedicle screw coupled to the nitinol rod, respectively.
Figure 4B:
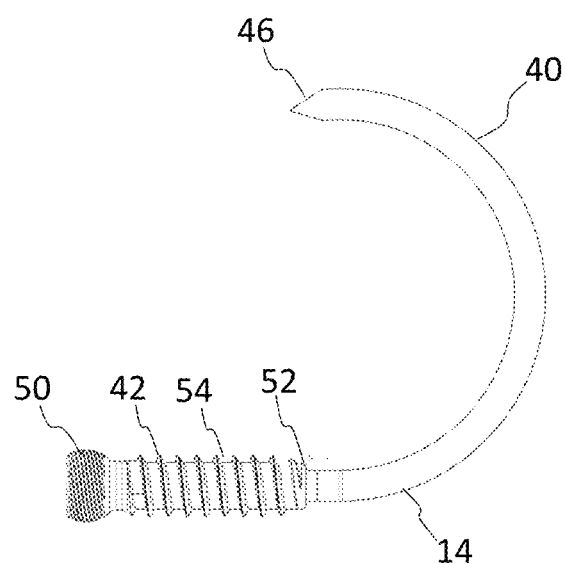

Turning now to FIGS. 3 and 4A-4B, the pedicle-based fixation implant 14 may be made up of two biocompatible components: a rod 40 and a screw 42. The rod 40 may be composed of nitinol or other shape-memory material, which allows the rod 40 to bend into a curved state upon deployment. The nitinol rod 40 may include a proximal end 44 configured to mate with the pedicle screw 42 and a distal end 46 configured to engage bone. The super elasticity of nitinol allows for the material to be drawn into a straight configuration from its naturally curved state. In its relaxed state, the nitinol rod 40 may have a curve or arc of 180° or a curve or arc up to 180°. The body of the nitinol rod 40 may have a polygonal cross-section with planar faces. For example, the body may have a quadrilateral cross-sectional shape, such as a square. The distal end 46 may include a pointed or sharp tip configured to pierce bone. The proximal end 44 may include a threaded portion 48 which mates with the screw 42. The nitinol rod 40 may be deployed through the pedicle 8 of the inferior vertebra 2 and the distal end 46 may pass through the vertebral body 6 of the inferior vertebra 2, through the disc space 4, and into the vertebral body 6 of the superior vertebra 2.

The screw 42 may include a pedicle screw that extends from a proximal end with a screw head 50 to a distal end with a tip 52 configured to engage the nitinol rod 40. The screw 42 may be comprised of titanium or any suitable biocompatible material. The screw head 52 may define a drive recess that can be engaged by a screw-driving instrument or other device. The screw head 50 may have any general shape. In the embodiment shown, the screw head 50 has a curved or spherical surface that is threaded or roughened. The screw head 50 may interface with a polyaxial tulip head, which may retain a spinal rod. Examples of tulip heads and rod constructs are described in more detail, for example, in U.S. Pat. No. 10,368,917, which is incorporated by reference herein in its entirety for all purposes. The screw 42 has a threaded shaft 54 configured to engage bone. It will be appreciated that the threaded shaft 54 may have a number of different features, such as lead(s), thread pitch, thread angle, shaft diameter to thread diameter, overall shaft shape, and the like. It is also contemplated that the threaded shaft 54 could be substituted with another suitable bone fastener, such as an anchor, clamp, or the like configured to engage bone.

The threaded shaft 54 of the pedicle screw 42 may define a hollow body for receiving the proximal end 44 of the nitinol rod 40. The hollow body may extend along a portion or the entire length of the screw 42. The hollow body defines an internal threaded portion configured to mate with the outer threaded portion 48 of the nitinol rod 40. It will be appreciated that one or more additional features may be used to lock the screw 42 to the nitinol rod 40, such as a snap ring within the pedicle screw 42 configured to snap into an external groove 56 of the nitinol rod 40. The pedicle screw 42 may be deployed through the same pedicle 8 of the inferior vertebra 2 as the nitinol rod 40. The pedicle screw 42 is inserted and driven over the proximal threads 48 of the nitinol rod 40 to purchase the existing cortical bone in the pedicle 8 and anchor the proximal end 44 of the nitinol rod 40 to the inferior pedicle 8.

Figure 5:
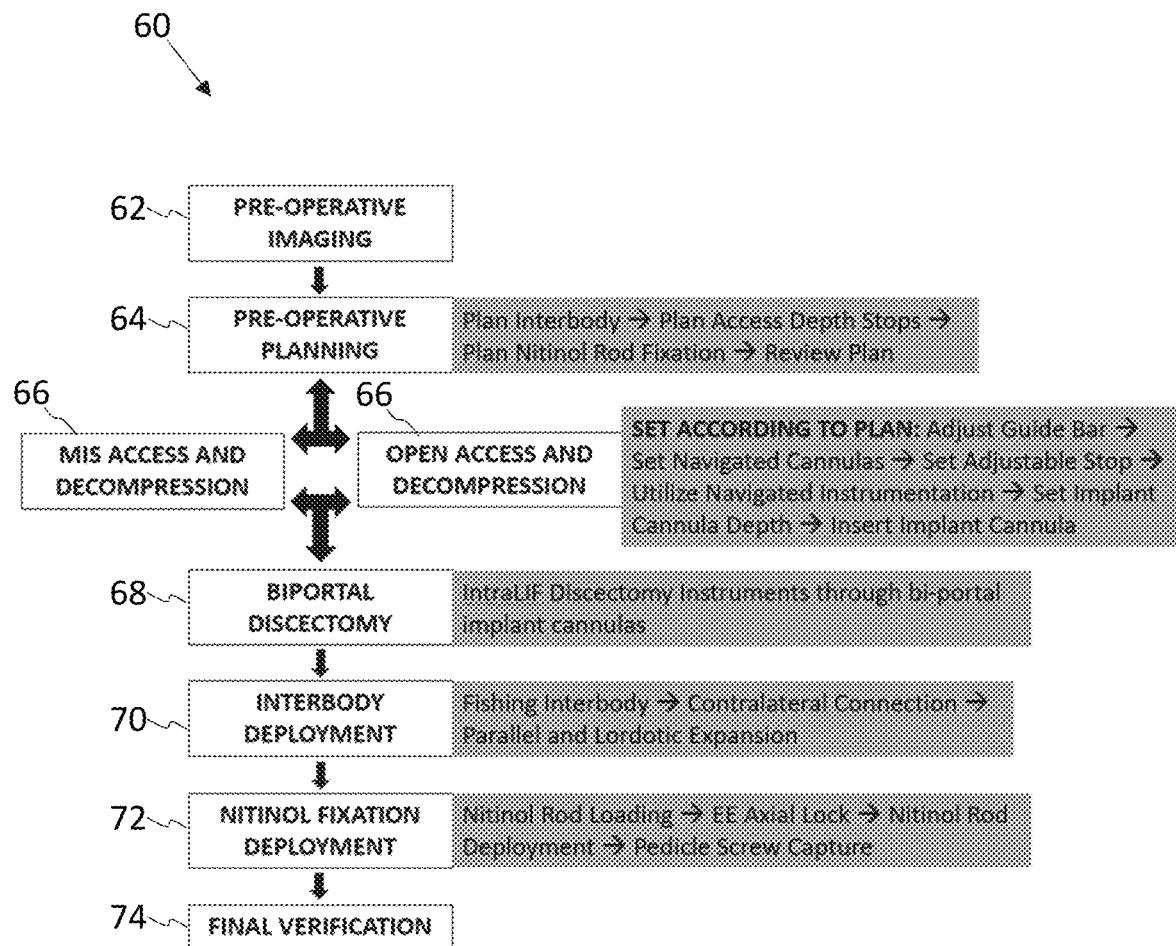
FIG. 5 is a flowchart of a workflow for a bi-portal lumbar interbody fusion procedure according to one embodiment.

Turning now to FIG. 5, the interlaminar lumbar interbody fusion procedure may have a structured workflow 60 for preparing and installing the expandable interbody implant 12 and pedicle-based fixation implants 14. The workflow 60 may include one or more of the following steps. (1) Pre-operative imaging 62 may be performed of the patient anatomy, such as CT (computed tomography), MRI (magnetic resonance imaging), or other relevant imaging. (2) Pre-operative planning 64 may provide for planned placement of the expandable interbody 12, planned access paths, planned placement of the nitinol rod fixation devices 14, and a review of the plan strategy. (3) Access and decompression 66 of the disc space 4 may be set according to the plan. The disc space 4 may be accessed through a MIS (minimally invasive surgery) or open surgery. The access may utilize navigated instrumentation and/or robotic assistance. (5) A bi-portal discectomy 68 may be performed to increase the efficiency and overall quality of soft tissue removal. (6) Interbody deployment 70 may include deploying, positioning, articulating, and expanding the implant 12. (7) Nitinol fixation deployment 72 may include deploying the pedicle-based intradiscal fixation implants 14 through the pedicles 8 of the inferior vertebra 2 and into the vertebral body 6 of the superior vertebra 2. (8) Final verification 74 may include checking the location of the interbody and pedicle-based fixation implants 12, 14 and ensuring the final construct is accomplishing the pre-operative plan and achieving the desired correction. The workflow 60 may be assisted and enhanced using imaging, navigation and/or robotics.

Figure 6A:
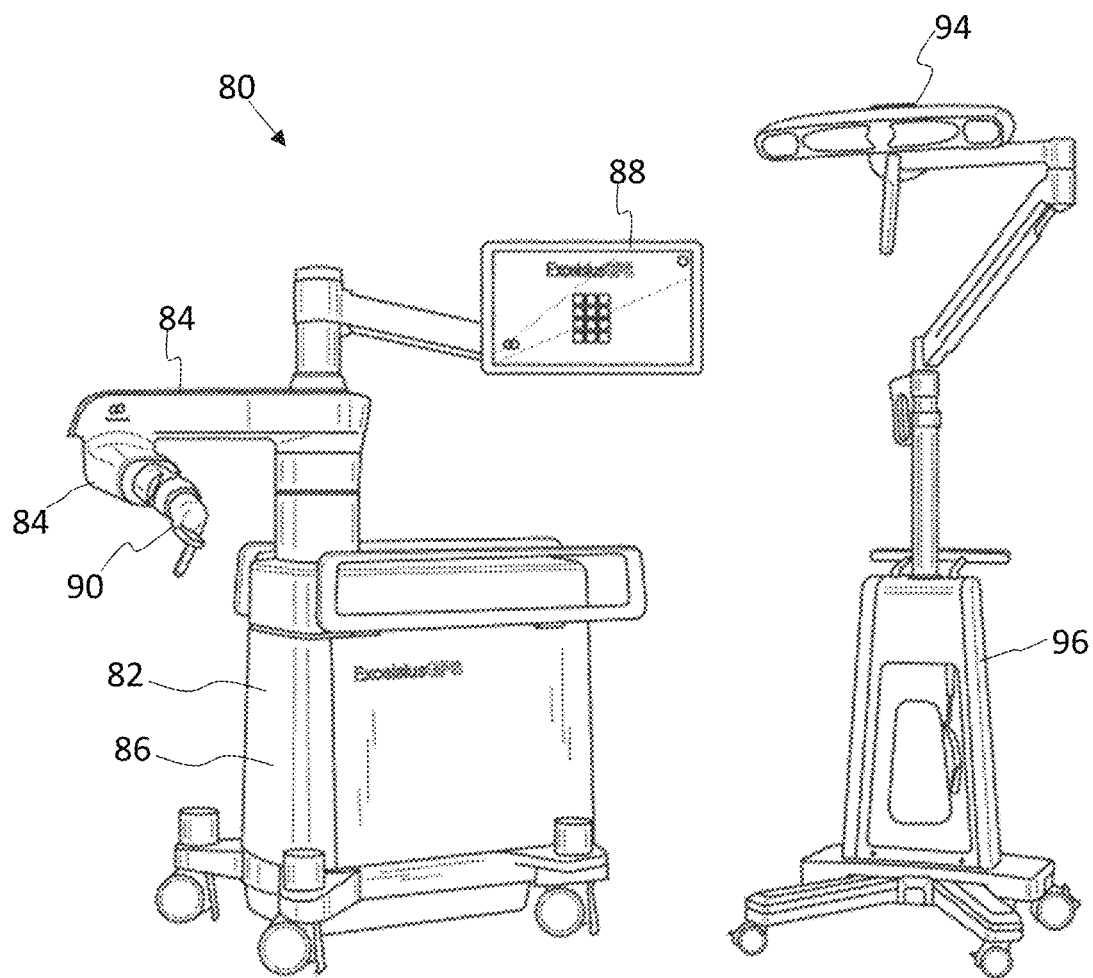
FIGS. 6A-6B depict a robotic surgical system including an end-effector with a guide tube according to one embodiment.
Figure 6B:
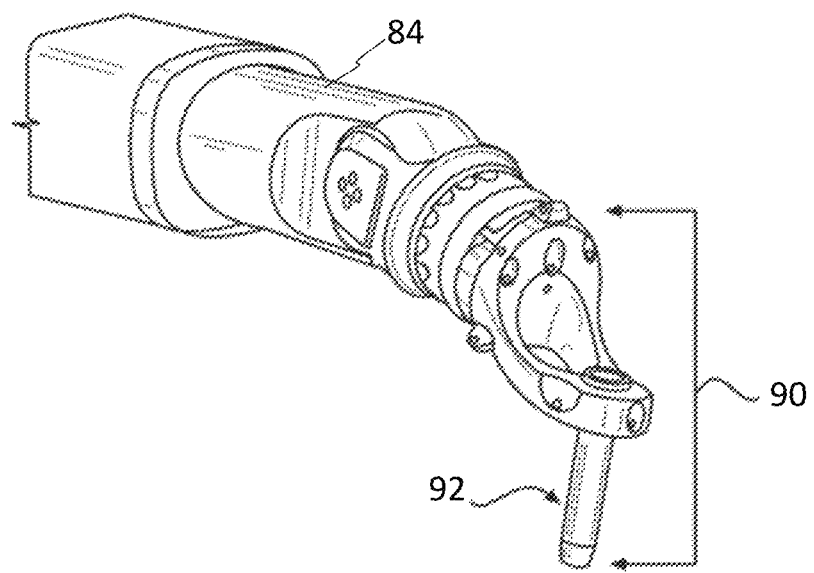
Figure 7:
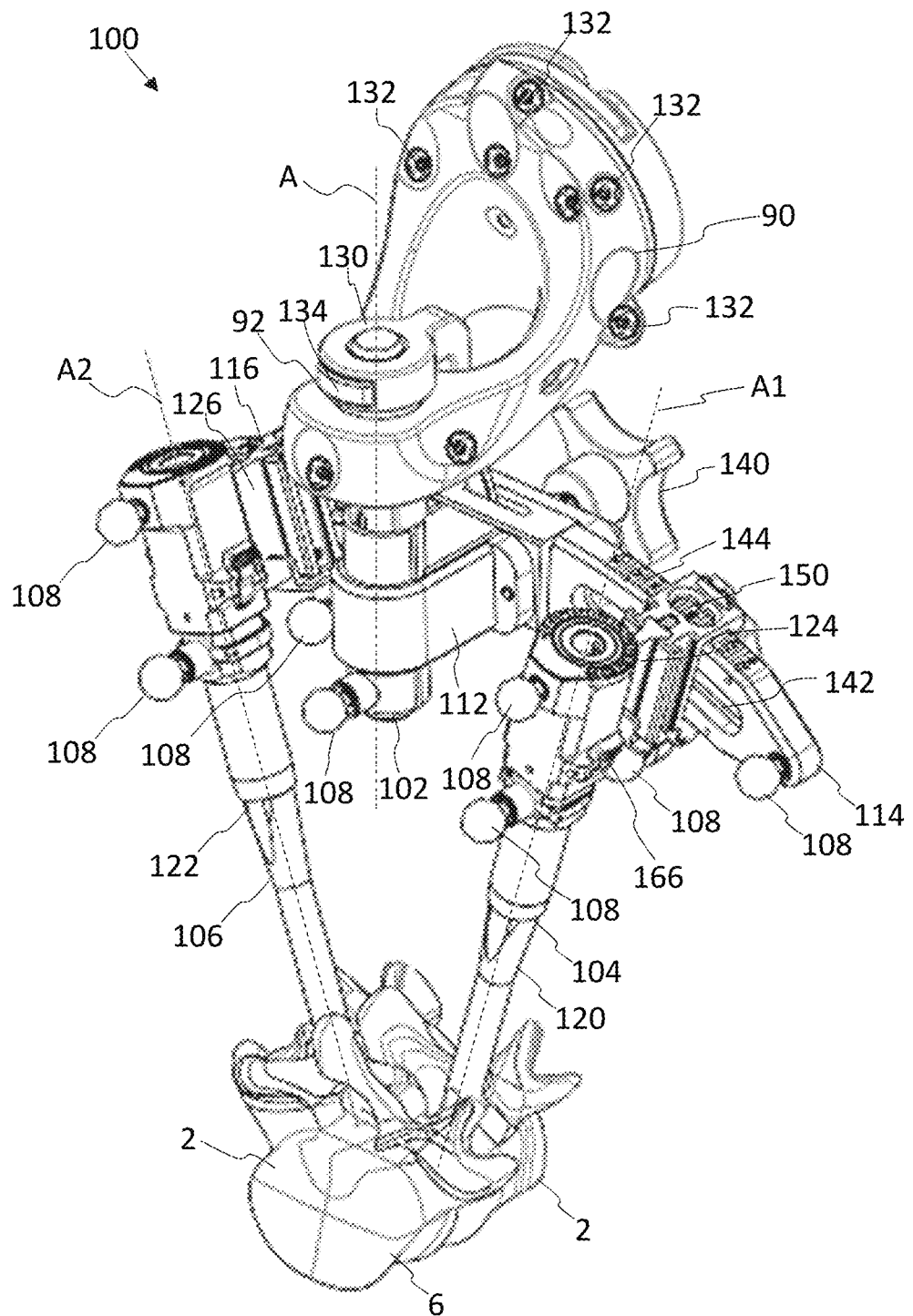
FIG. 7 shows a perspective view of a robotically-enabled bi-portal posterior access assembly received in the guide tube of the end-effector of FIG. 6B according to one embodiment.

FIGS. 6A-6B illustrate an example of a surgical robotic and navigation system 80. The surgical robot system 80 may include, for example, a surgical robot 82, a base 86 including a computer, a display or monitor 88 (and optional wireless tablet) electronically coupled to the computer, one or more robot arms 84 controlled by the computer, and an end-effector 90 including a guide tube 92 electronically coupled to the robot arm 84. The surgical robot system 80 may also utilize a camera 94, for example, positioned on a separate camera stand 96. The camera stand 96 can have any suitable configuration to move, orient, and support the camera 94 in a desired position. The camera 94 may include any suitable camera or cameras, such as one or more infrared cameras (e.g., bifocal or stereophotogrammetric cameras), able to identify, for example, active and/or passive tracking markers in a given measurement volume viewable from the perspective of the camera 94. The camera 94 may scan the given measurement volume and detect the light that comes from the markers in order to identify and determine the position of the markers in three-dimensions. For example, active markers may include infrared-emitting markers that are activated by an electrical signal (e.g., infrared light emitting diodes (LEDs)), and passive markers may include retro-reflective markers that reflect infrared light (e.g., they reflect incoming IR radiation into the direction of the incoming light), for example, emitted by illuminators on the camera 94 or another suitable device.

The surgical robot 82 is able to control the translation and orientation of the end-effector 90. The robot 82 may be able to move end-effector 90 along x-, y-, and z-axes, for example. The end-effector 90 can be configured for selective rotation about one or more of the x-, y-, and z-axis, and a Z Frame axis (such that one or more of the Euler Angles (e.g., roll, pitch, and/or yaw) associated with end-effector 90 can be selectively controlled). In some exemplary embodiments, selective control of the translation and orientation of end-effector 90 can permit performance of medical procedures with significantly improved accuracy.

The robotic positioning system 82 includes one or more computer controlled robotic arms 84 to assist the surgeon in planning the position of one or more navigated instruments relative to intraoperative patient images. The system 80 includes 2D & 3D imaging software that allows for preoperative planning, navigation, and guidance through a dynamic reference base, navigated instruments, and positioning camera 94 for the placement of spine, orthopedic, or other devices. Further examples of surgical robotic and/or navigation systems can be found, for example, in U.S. Pat. Nos. 10,675,094 and 9,782,229, which are incorporated by reference herein in their entireties for all purposes.

Turning now to FIGS. 7 and 8A-8C, a bi-portal posterior access system and technique is shown, which may be robotically-enabled to assist a surgeon during surgery. A bi-portal assembly 100 may be configured to attach to the guide tube 92 of the end-effector 90 of the robot 82. In this manner, the robot 82 is configured to control the location and orientation of the bi-portal assembly 100 relative to the surgical area. The bi-portal assembly 100 includes a guide bar assembly 102, a first navigated cannula assembly 104, and a second navigated cannula assembly 106. The entire bi-portal assembly 100 is configured to pivot or rotate about the central longitudinal axis A of the guide tube 92 of the end-effector 90. The first and second navigated cannula assemblies 104, 106 are each configured to independently angulate with respect to the central longitudinal axis A, thereby providing the desired access trajectories to the surgical area. The bi-portal assembly 100 may include a plurality of tracking markers 108 configured to monitor the various features of the bi-portal assembly 100 and provide navigated and/or robotic assistance during the surgery.

Figure 8A:
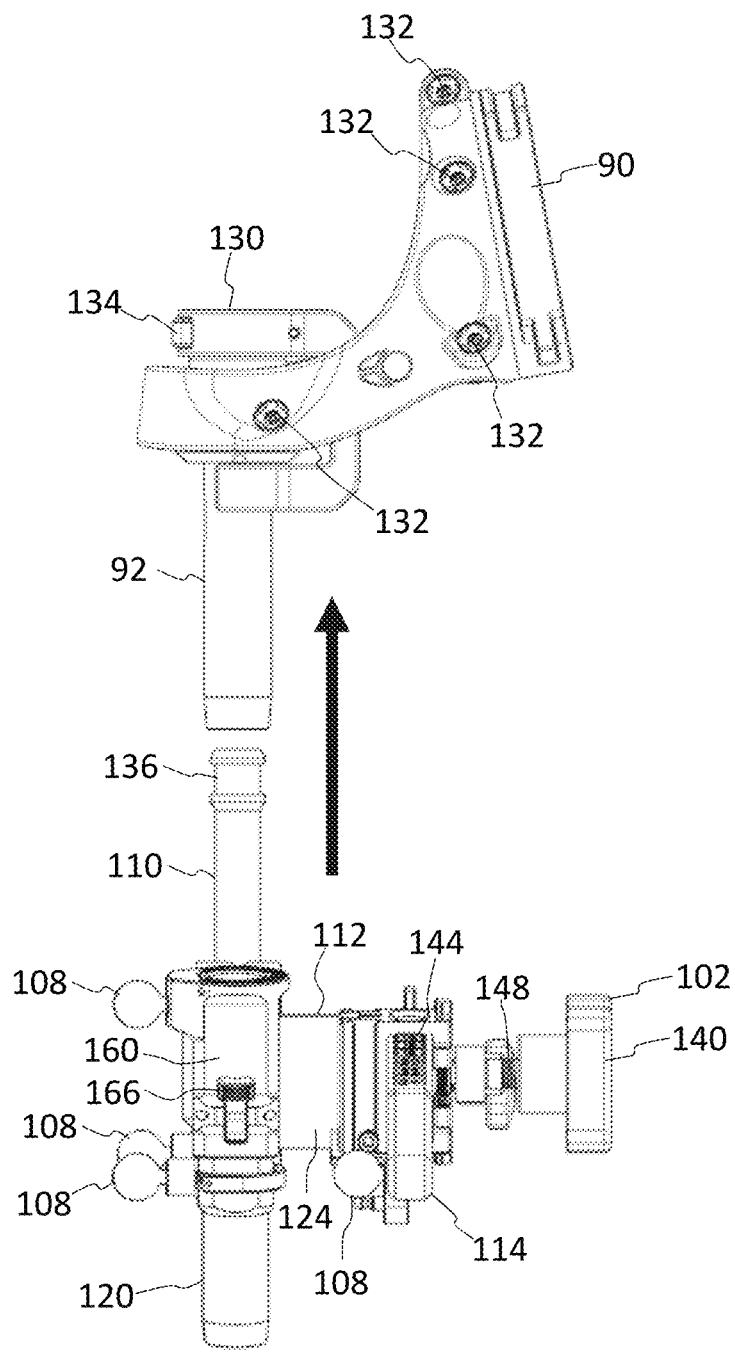
FIGS. 8A-8C show a method of attaching the guide bar assembly of the bi-portal assembly to the guide tube of the end-effector, rotating the bi-portal assembly, and aligning the bi-portal assembly for access to the spine according to one embodiment.

As best seen in FIG. 8A, the guide bar assembly 102 includes a central guide bar 110 configured to be inserted into the bottom of the guide tube 92 of the end-effector 90. The guide bar assembly 102 includes a central support arm 112 for holding first and second lateral wings 114, 116. The first and second lateral wings 114, 116 are positioned on opposite sides of the guide bar 110 and extend outwardly in opposite directions from one another. The first lateral wing 114 supports a first navigated cannula 120 via a first supporting arm 124 and the second lateral wing 116 supports a second navigated cannula 122 via a second supporting arm 126. The navigated cannulas 120, 122 each include a long hollow tubular body defining a central longitudinal axis A1, A2, respectively. Each navigated cannula 120, 122 is configured to guide an instrument placed through the respective cannula 120, 122 along the desired trajectory to the surgical site.

With further emphasis on FIG. 8A, the guide bar 110 is configured to slide into and lock axially to the guide tube 92 of the end-effector 90. For example, the guide bar 110 may snap into an axial locking cap 130. The axial locking cap 130 may be snapped on an inside portion of the end-effector 90 to avoid blocking the infrared LEDs 132, which act as tracking markers for the end-effector 90. An upper portion of the locking cap 130 may rest on a top surface of the end-effector 90 above the guide tube 92. The locking cap 130 may include a locking button 134 configured to engage with a groove 136 of the guide bar 110. The groove 136 may be located between two annular rings at the proximal end of the guide bar 110. The locking button 134 may be spring-loaded to automatically engage the groove 136 when the guide bar 110 is slid upwards through the inner diameter of the guide tube 92 of the end-effector 90. When locked with the locking cap 130, the guide bar assembly 102 is axially constrained to the guide tube 92, but is still permitted to rotate about the longitudinal axis A of the guide tube 92. Alternatively, the locking connection to the end-effector 90 of the robot 82 could be built into the guide bar 110 rather connecting through the end-effector 90. It will be appreciated that other suitable locking mechanisms may also be utilized.

Figure 8B:
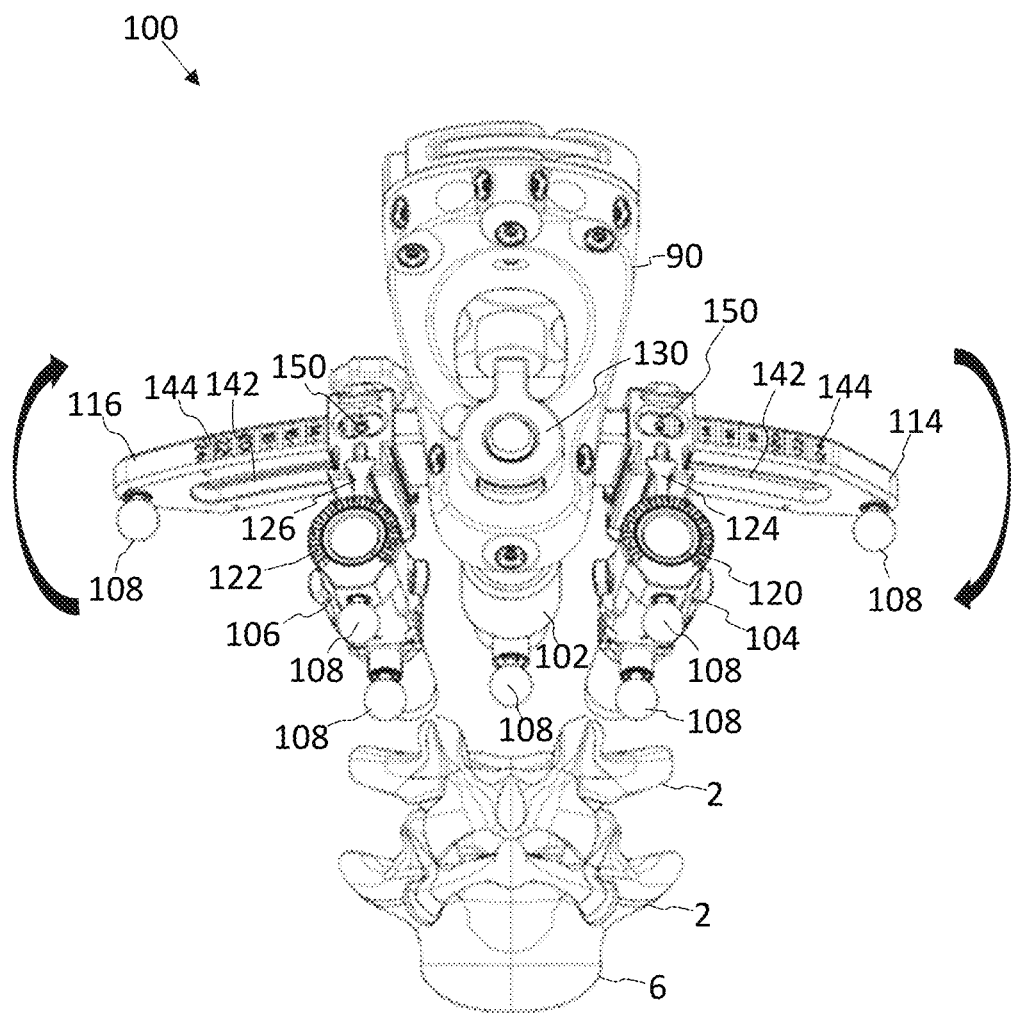
Figure 8C:
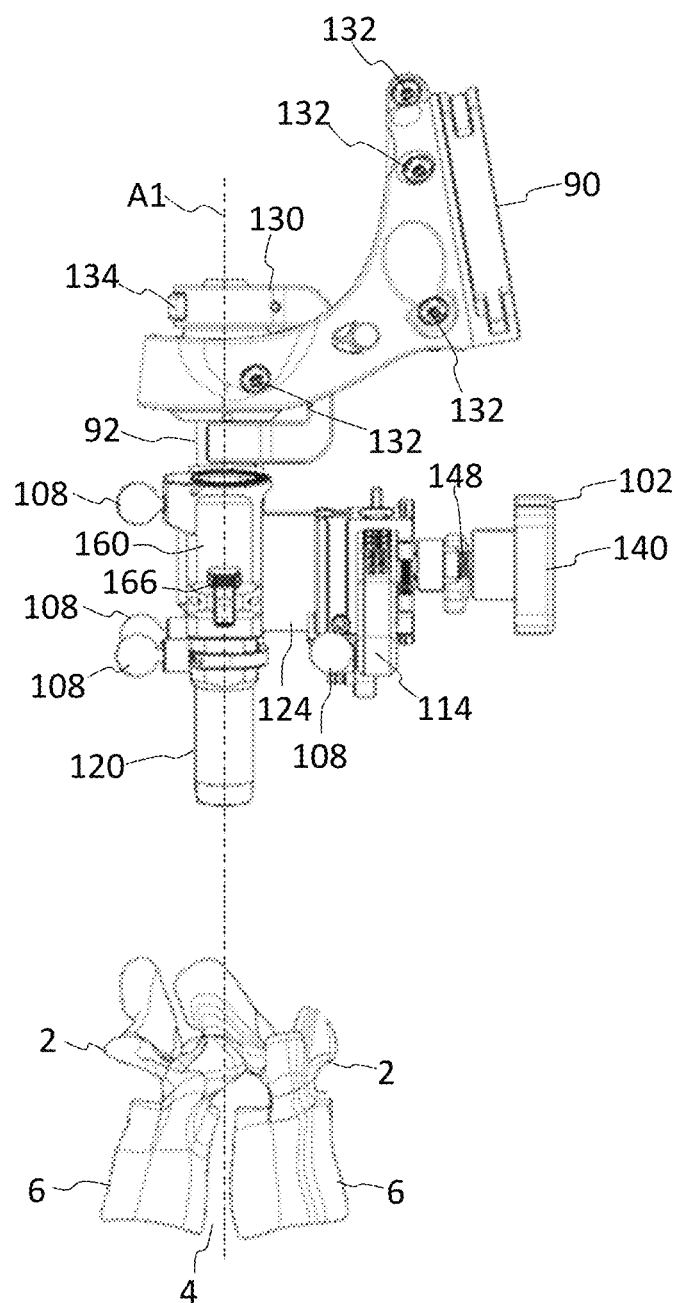

After the guide bar assembly 120 is axially locked to the end-effector 90, the guide bar assembly 120 may be rotated to the desired location. As shown in FIG. 8B, the first and second lateral wings 114, 116 may be rotated about the longitudinal axis A of the guide tube 92. Once the desired rotational position is obtained, the rotational movement of the assembly 102 may be fixed with a central wheel handle lock 140. The central wheel handle lock 140 may have a threaded stud 148 mounted into a threaded hole in the guide bar assembly 120. Rotation of the central wheel handle lock 140 tightens, holds, and locks the final position of the guide bar assembly 120. It will be appreciated that another suitable lock may also be utilized to secure the guide bar assembly 120.

Figure 9A:
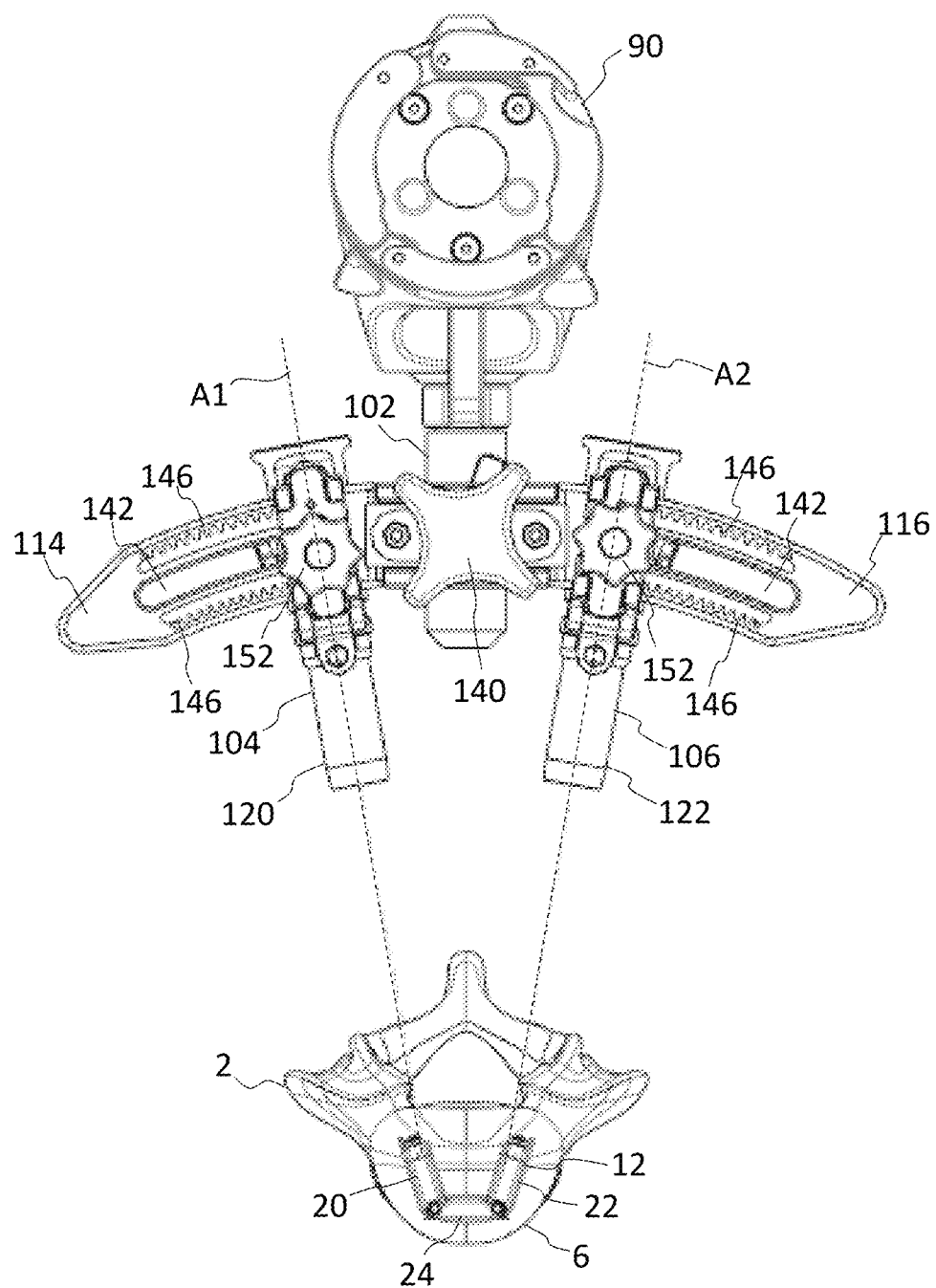
FIGS. 9A-9B depict rear views of the bi-portal assembly showing adjustment of the width and angles of the cannulas for installation of the expandable interbody implant according to one embodiment.
Figure 9B:
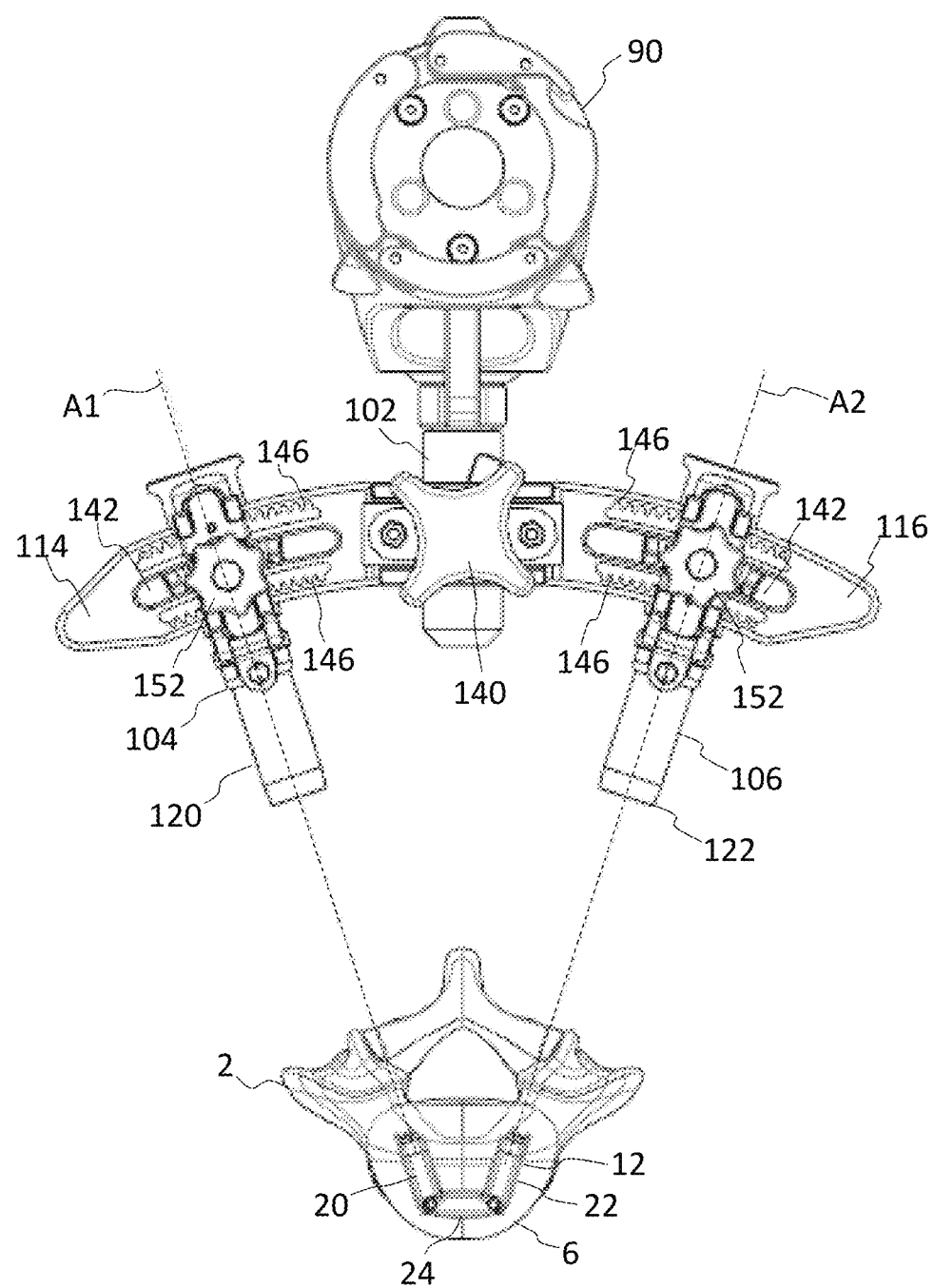
Figure 10:
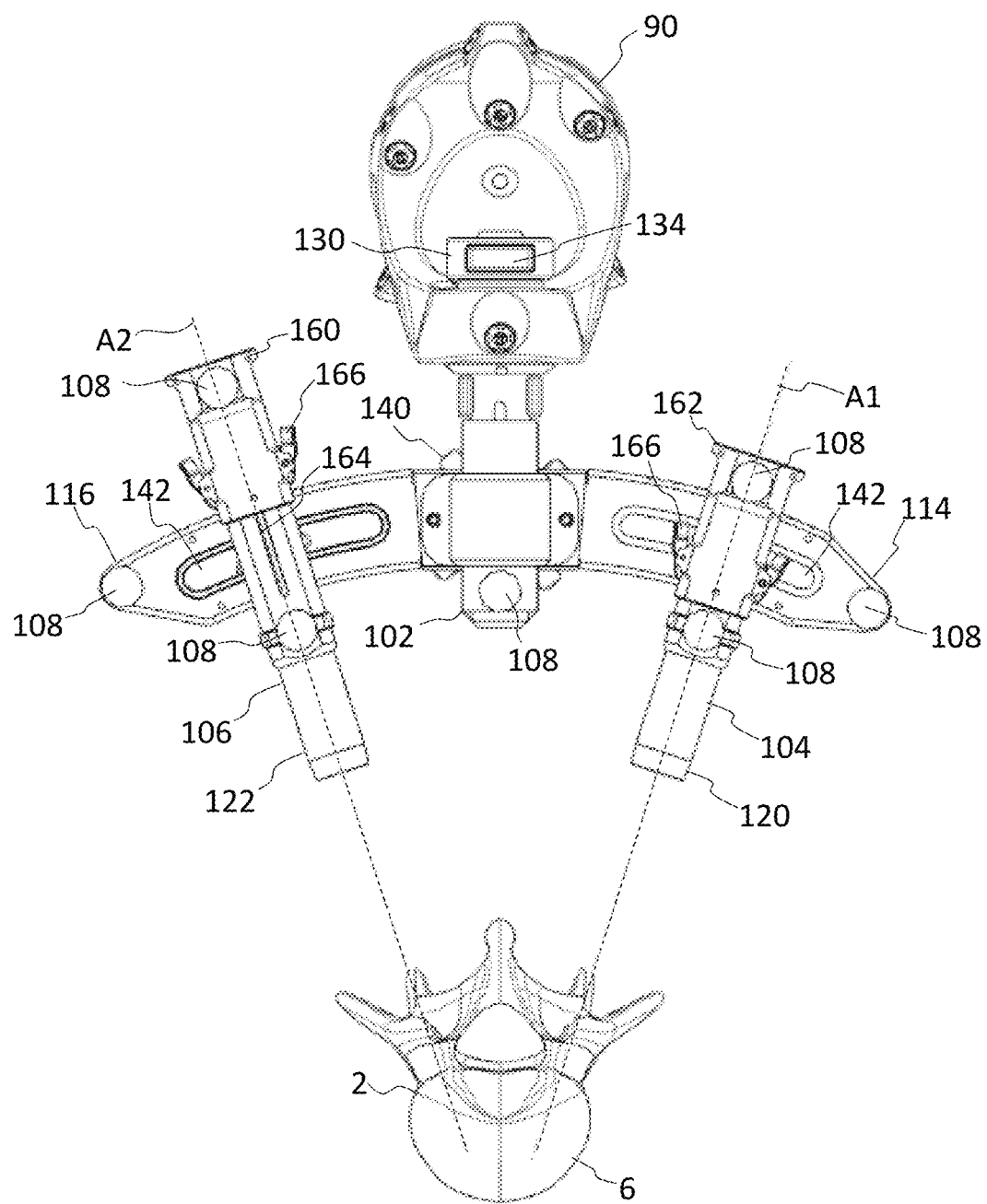
FIG. 10 shows a front view of the bi-portal assembly with adjustable stops for controlling the access depth of an instrument through the cannulas according to one embodiment.

With emphasis on FIGS. 9A-9B, after the rotational position has been locked, the width and/or angulation of the first and second navigated cannulas 120, 122 may be independent adjusted. The first and second lateral wings 114, 116 may be curved or angled to allow for angular adjustments of the cannulas 120, 122 as the cannulas 120, 122 move along the lateral wings 114, 116. For example, the first and second lateral wings 114, 116 may be curved or angled such that the terminal ends of the wings 114, 116 point downwards, thereby providing for a greater degree of angulation as the cannulas 120, 122 move further from the central guide bar 110.

Each of the first and second lateral wings 114, 116 may include an elongate slot 142 for securing the respective first and second navigated cannula assemblies 104, 106. The navigated cannula assemblies 104, 106 may slide along the respective slots 142 to adjust the width and/or angulation of the cannulas 120, 122. As best seen in FIG. 8B, a top surface of the wings 114, 116 may each include graduations, an indicator scale, or other markings 144 to provide visual feedback on the distance and/or angle of the cannulas 120, 122. For example, each graduated scale 144 may range from 10-24° in increments of 2° for each cannula 120, 122. An opening 150 in the top face of support arm 124, 126 of the cannula assembly 104, 106 may provide an exact reading of the graduated marking on the indicator scale 144.

The cannula assemblies 104, 106 may move along one or more ratchets 146. The ratchets 146 may include linear or curvilinear ratchets 146 configured to mimic the shape of the lateral wings 114, 116. The ratchets 146 may be positioned above and below the elongate slots 142. The ratchets 146 may include a rack and pinion system for independently moving the cannula assemblies 104, 106 along the lateral wings 114, 116. The ratchets 146 may provide for incremental adjustment of the width and/or angle of the cannulas 120, 122. For example, the angle of the first cannula 120 may be aligned to match the desired location of the first lateral leg 20 of the implant 12 and the angle of the second cannula 122 may be aligned to match the desired location of the second lateral leg 22 of the implant 12. In addition, the width between the first and second cannulas 120, 122 may be matched to the desired width between the lateral legs 20, 22 of the implant 12. The width and/or angle of the cannulas 120, 122 may each be independently locked with a rotatable knob 152. Rotation of each of the knobs 152 tightens, holds, and locks the final position of each of the cannulas 120, 122. It will be appreciated that any suitable lock may be utilized to secure the cannulas 120, 122.

The bi-portal assembly 100 may include a plurality of tracking markers 108, such as passive spherical markers, configured to monitor the position of the guide bar assembly 102 and first and second navigated cannula assemblies 104, 106, respectively. In the embodiment shown, nine markers 108 are used to track the locations and positions of the components, but it will be appreciated that any suitable number and configuration of markers may be selected. The distal end of the guide bar 110 may include a first tracking marker 108. The terminal end of first lateral wing 114 may include a second tracking markers 108 and the terminal end of the second lateral wing 116 may include a third tracking marker 108. The bottom of the first supporting arm 124 may include a fourth tracking marker 108 and the bottom of the second supporting arm 126 may include a fifth tracking marker 108. The first navigated cannula 120 may include sixth and seventh tracking markers 108 aligned along the central longitudinal axis A1 of the cannula 120. The second navigated cannula 122 may include eighth and ninth tracking markers 108 aligned along the central longitudinal axis A2 of the cannula 122. In this manner, the tracking markers 108 are configured to provide information to the robot system 80 regarding the cannulas 120, 122 and the bi-portal assembly 100, such as the location, orientation, distance, angles, and other relevant information.

Turning now to FIGS. 10, 11A-11B, and 12A-12B, each cannula assembly 104, 106 may include an adjustable stop 160, 162 configured to set the access depth into the surgical site. Depth control may be set independently for each of the trajectories for customized access, for example, for abnormal patient anatomy. Each stop 160, 162 may include a sleeve or tubular body configured to slide over or along the respective cannula 120, 122. The stop 160, 162 may slide along an elongate slit 164 extending along the central longitudinal axis A1, A2 of the cannula 120, 122. A pin or other engagement member from the stop 160, 162 may be receivable in the slit 164 to guide the stop 160, 162 to the desired depth. The depth may be locked with a lever latch 166. The lever latch 166 may include a pair of pivotable thumb latches positioned on opposite sides of the cannula 120, 122. When depressed and squeezed together, the lever latch 166 allows the depth stop 160, 162 to slide along the length of the cannula 120, 122. When released, the lever latch 166 locks the position of the depth stop 160, 162, thereby providing a maximum access depth for any instruments placed through the cannula 120, 122. For the embodiment shown in FIG. 10, the right trajectory along axis A1 provides for deeper access to the disc space 4 than the left trajectory along axis A2. It will be appreciated that the stops 160, 162 may be independently adjusted to provide the same or different access depths. Alternatively, instead of manual control, the robot 82 may control and auto-generate the width, angulation, and/or adjustable depth control settings for the cannulas 120, 122.

Figure 11A:
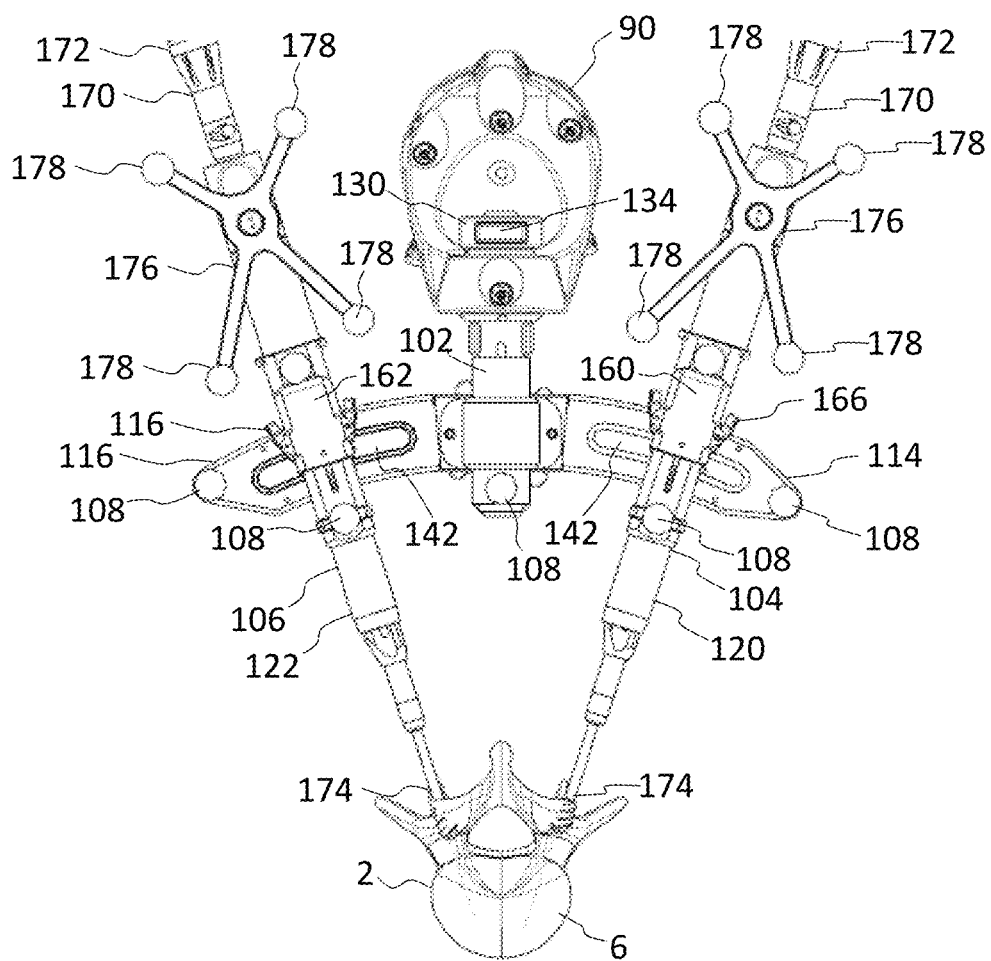
FIGS. 11A-11B show front and side views, respectively, of the bi-portal assembly with navigated instruments positioned through the cannulas to access the disc space according to one embodiment.
Figure 11B:
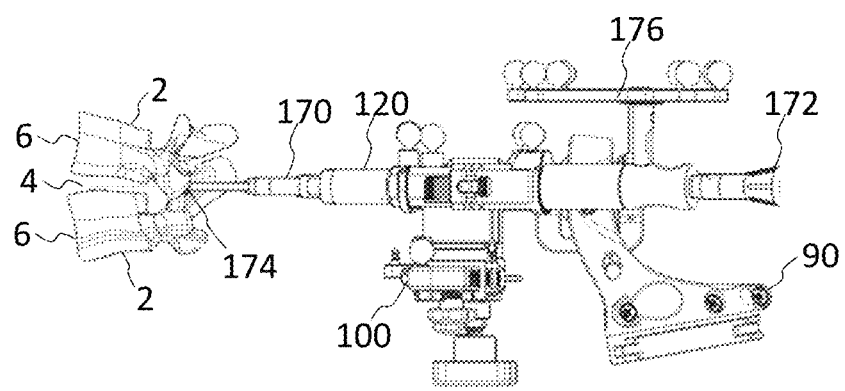
Figure 12A:
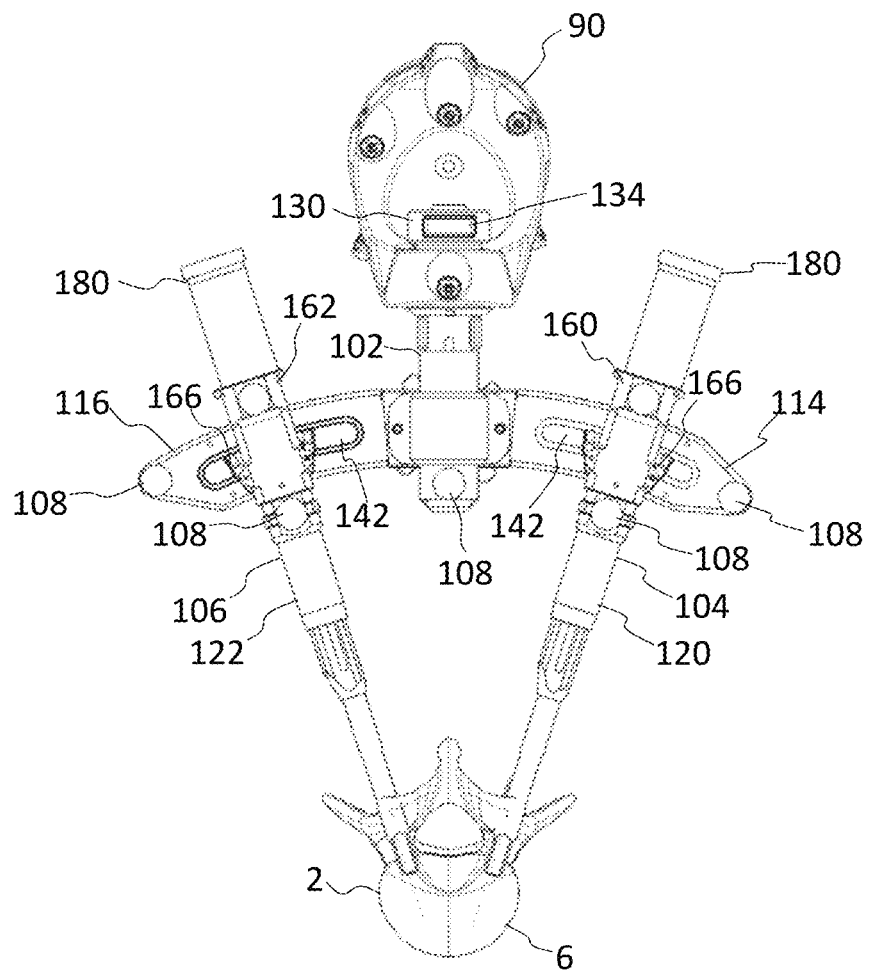
FIGS. 12A-12B show front and side views, respectively, of the bi-portal assembly with alternative instruments positioned through the cannulas to access the disc space according to one embodiment.
Figure 12B:
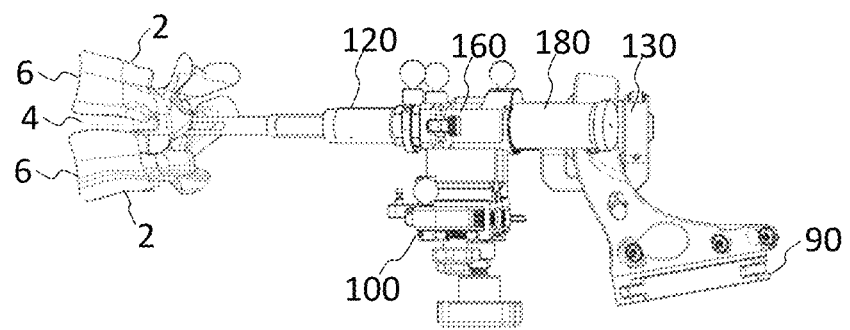

With emphasis on FIGS. 11A-11B, a navigated instrument 170 may be positioned through each cannula 120, 122 to access the surgical site. The navigated instrument 170 may extend from a proximal end 172 with a handle configured to be gripped by a user to a distal end 174 with a tip configured to access the surgical site. The navigated instrument 170 may include an array 176 with a plurality of tracking markers 178, such as spherical passive markers, configured to identify and monitor movement of the instrument 170 by the navigation and robotic system 80. The navigated instrument 170 may be compatible with dilators, off-center sheaths, docking facet dilators, and other instrumentation. FIGS. 12A-12B show instruments 180 positioned through cannulas 120, 122, respectively. The stops 160, 162 may be adjusted with the instrumentation 180 present. By removing the navigated array 176, instruments 180 may provide improved visualization of the surgical site.

Figure 13A:
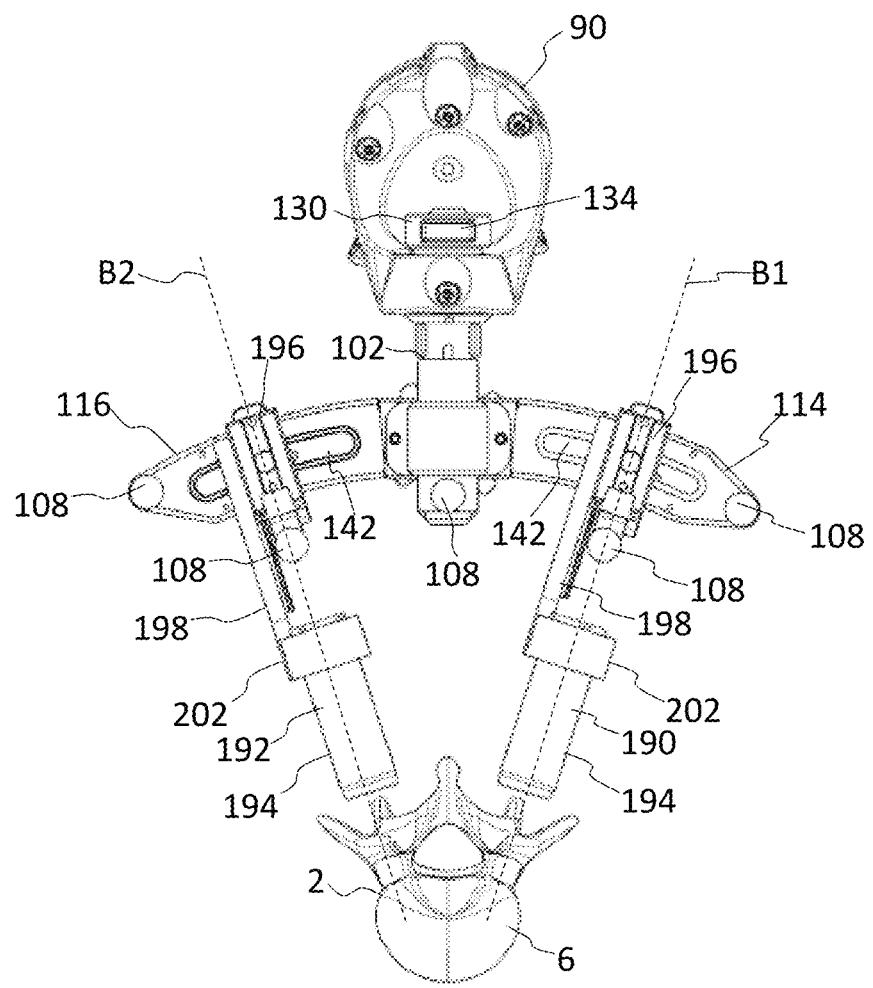
FIGS. 13A-13C show port assemblies connected to the guide bar assembly where width and angulation between the ports, conical angulation of the ports, and the depth of the ports may be adjusted to increase visualization to the surgical site according to one embodiment.
Figure 13B:
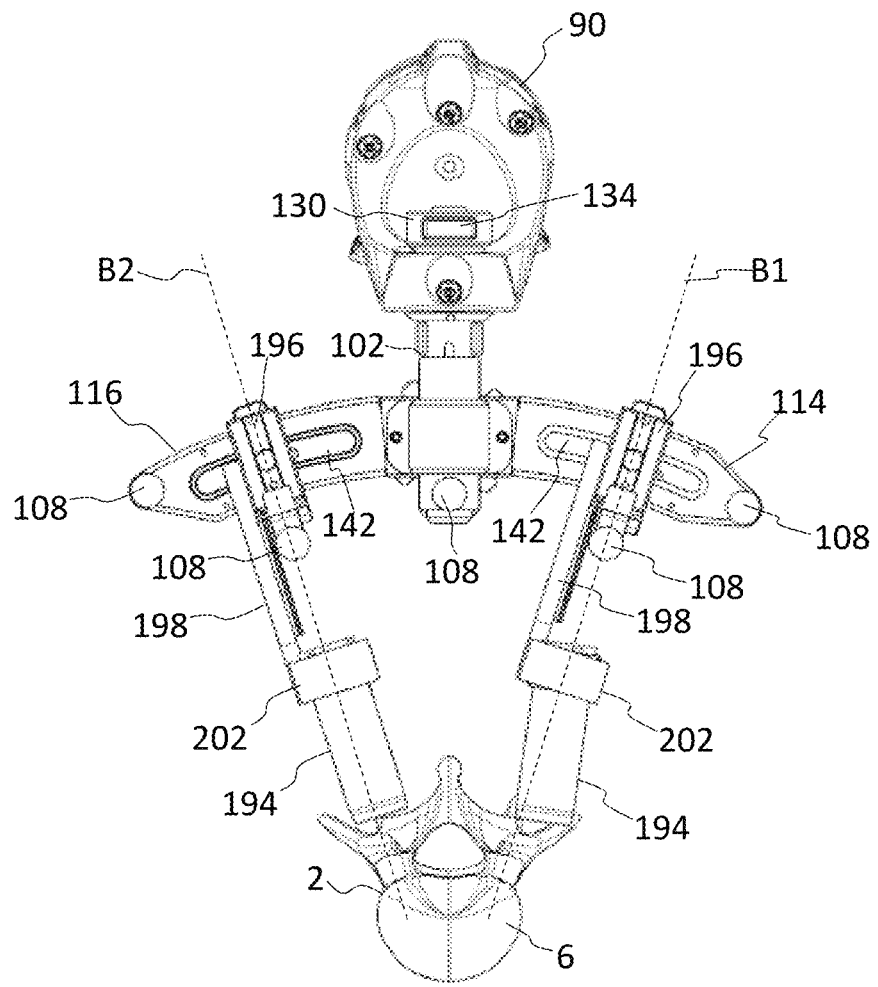
Figure 13C:
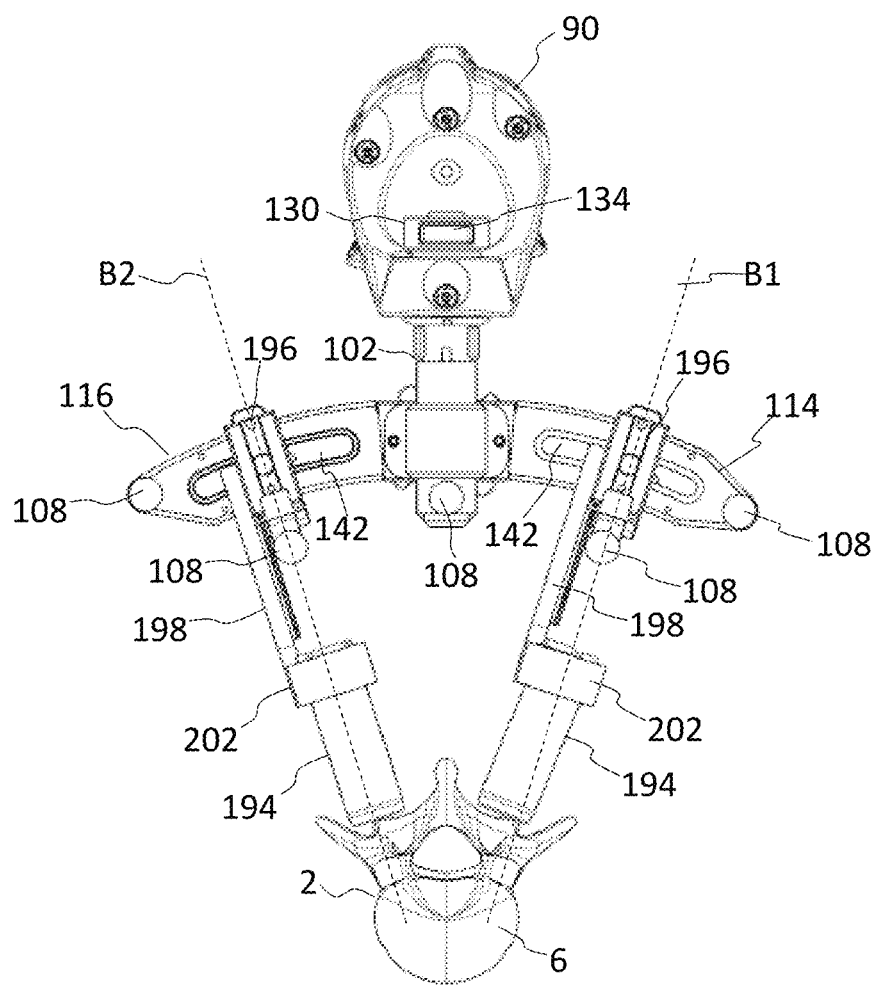
Figure 14A:
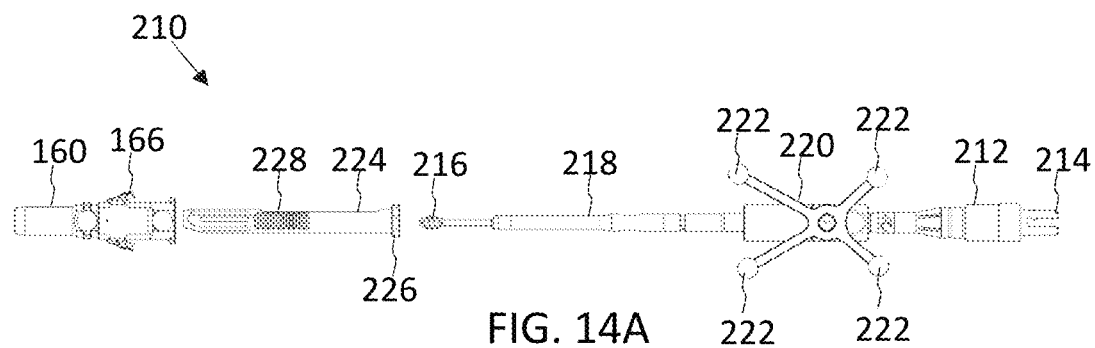
FIGS. 14A-14D show exploded and assembled views of a navigated instrument assembly with an adjustable stop for controlling the access depth according to one embodiment.
Figure 14B:
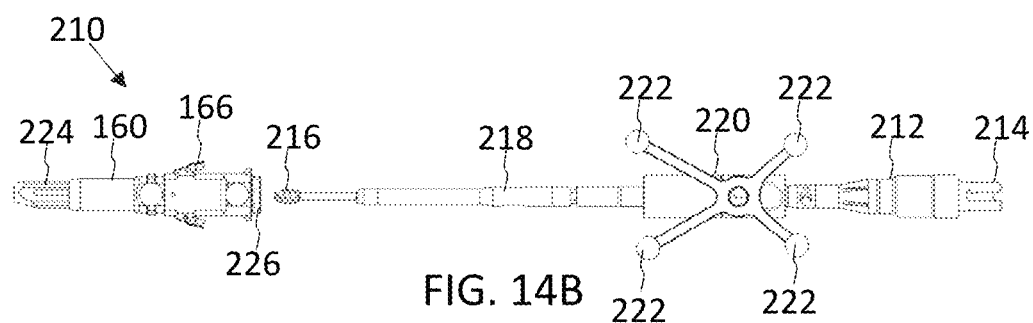
Figure 14C:
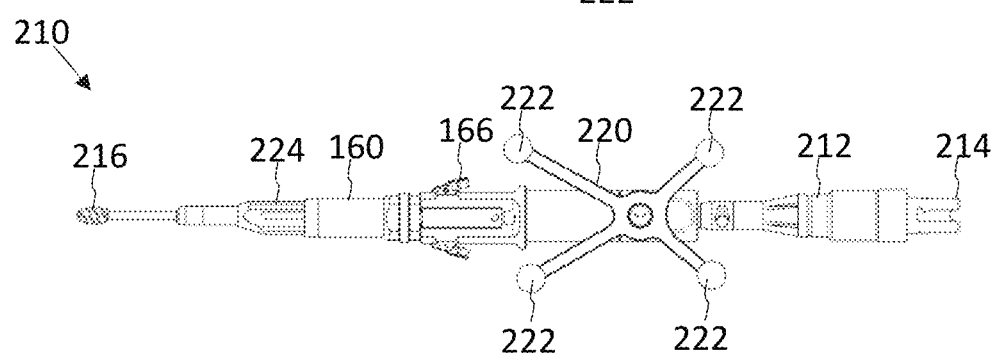
Figure 14D:
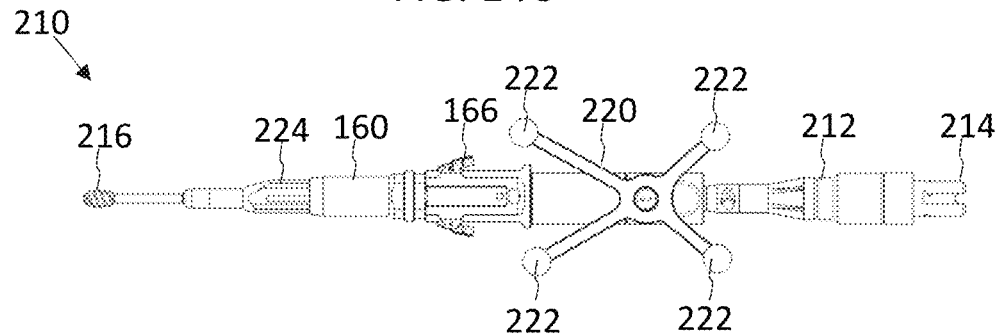

With emphasis on FIGS. 13A-13C, direct visualization port assemblies 190, 192 are shown according to one embodiment. The direct visualization port assemblies 190, 192 may replace the cannula assemblies 104, 106 to increase visualization of the neural elements during decompression. The first lateral wing 114 of the guide bar assembly 102 supports the first port assembly 190 and the second lateral wing 116 of the guide bar assembly 102 supports the second port assembly 192. Each of the port assemblies 190, 192 may include an access port 194, a moveable attachment assembly 196, and an extension arm 198 connecting the access port 194 to the attachment assembly 196. In the same manner as the cannula assemblies 104, 106, the attachment assemblies 196 may slide along the respective slots 142 through the first and second lateral wings 114, 116 to adjust the width and/or angulation between the port assemblies 190, 192. As shown in FIG. 13A, each attachment assembly 196 and access port 194 may be aligned along a central longitudinal axis B1, B2.

The access port 194 may include a hollow tubular body for accessing the surgical site. The port 194 may be attached to the distal end of the extension arm 198 with a collar 202 that provides for a pivotable joint at the proximal end of the access port 194. The collar 202 may have a conical, spherical, or other suitable interface with the port 194 to allow for independent angulation of the port 194. As shown in FIG. 13B, the right port 194 is able to angulate laterally outward and off-axis of longitudinal axis B1. In FIG. 13C, the right port 194 is able to angulate inwardly toward mid-line but still off-axis of longitudinal axis B1. It will be appreciated that both the left and right ports 194 have independent angulation based on the desired access to the surgical site. The depth of the ports 194 may also be controlled via the extension arms 198. The extension arm 198 may translate the port 194 toward or away from the surgical site, thereby providing for customized adjustability of each of the ports 194. Accordingly, the width and angulation between the ports 194, the conical angulation of the ports 194, and the depth of the ports 194 may be adjusted to increase visualization and improve safety around the neural elements of the spine.

FIGS. 14A-14D depict a navigatable instrument assembly 210 according to one embodiment. The navigatable instrument assembly 210 may include an instrument 212 and adjustable stop 160. Although stop 160 is described, it will be appreciated that stop 162 is the same or another suitable stop may be substituted. The instrument 212 may include a body that extends from a proximal end 214 configured to attach to a powered handle to a distal end 216 having the instrument tip. The instrument tip 216 may include burrs, drills, osteotomes, reamers, or other suitable instruments for cutting and/or removing bone. The instrument 212 may be powered to provide for high-speed, oscillating, or other suitable powered tips 216. The shaft 218 of the instrument 212 may support an array 220 having a plurality of tracking markers 222, such as spherical passive markers, configured to identify and monitor movement of the instrument 212 by the navigation and robotic system 80. The shaft 218 of the instrument 212 is receivable through a securing sleeve 222 which attaches the adjustable stop 160 to the instrument 212. The securing sleeve 222 is positioned through the tubular body of the adjustable stop 160. The securing sleeve 222 includes an enlarged neck 226 at its proximal end configured to abut the proximal end of the stop 160 when received therethrough. The securing sleeve 22 includes one or more ribbed portions 228 configured to interface with the pivotable thumb latches of the lever latch 166, thereby securing the position of the stop 160. The instrument assembly 210 may be navigated alone or through a cannula, such as one of the navigated cannulas 120, 122, to perform the surgical procedure.

Figure 15A:
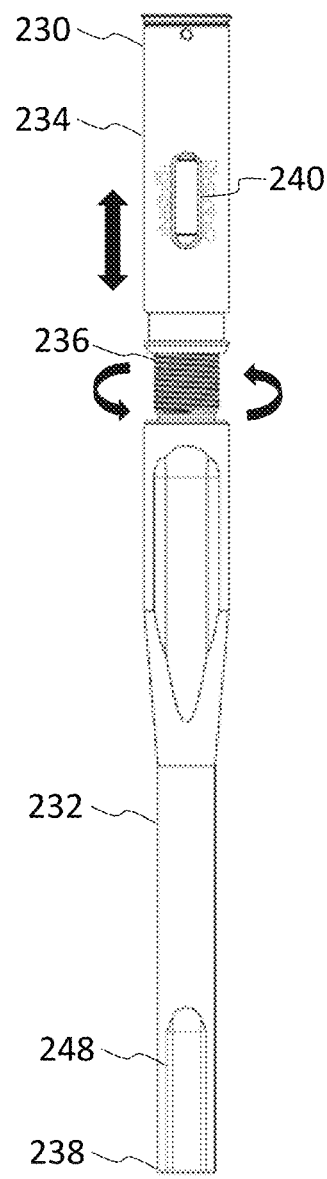
FIGS. 15A-15C show an adjustable implant cannula and a cannula dilator loaded in the implant cannula according to one embodiment.
Figure 15B:
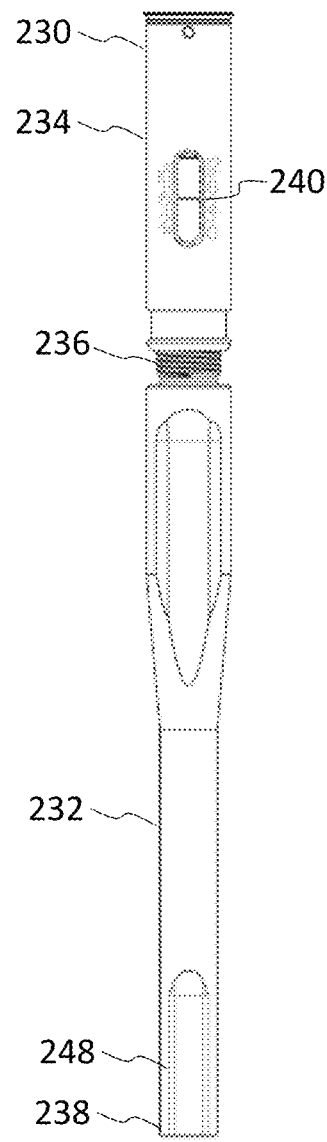
Figure 15C:
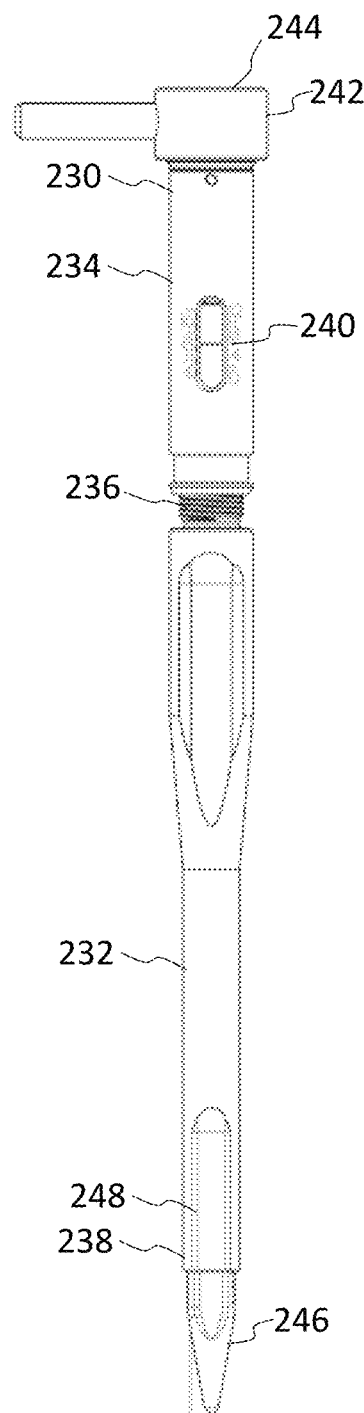

Turning now to FIGS. 15A-15C and 16A-16B, an adjustable implant cannula 230 is shown according to one embodiment. The adjustable implant cannula 230 includes a hollow cannula body 232 and an adjustable threaded cap 234. The cannula body 232 extends from a proximal end 236 to a distal end 238. The proximal portion 236 may be externally threaded to engage with the internally threaded cap 234. As the cap 234 is rotated the overall length of the implant cannula 230 is adjusted. An indicator 240 may be used to set the adjustable implant cannula 230 to a planned depth. The indicator 240 may include a window through the threaded cap 234 and a marking that can be aligned to a graduated value, such as between 0 and 12 in increments of 2. After the depth has been set, the cannula dilator 242 may be loaded into the implant cannula 230 as shown in FIG. 15C. The cannula dilator 242 may include a cap 244 at its proximal end and a distal tip 246 configured to expand. The distal tip 246 of the cannula dilator 242 may be keyed into a corresponding recess 248 at the distal end 238 of the cannula body 232.

Figure 16A:
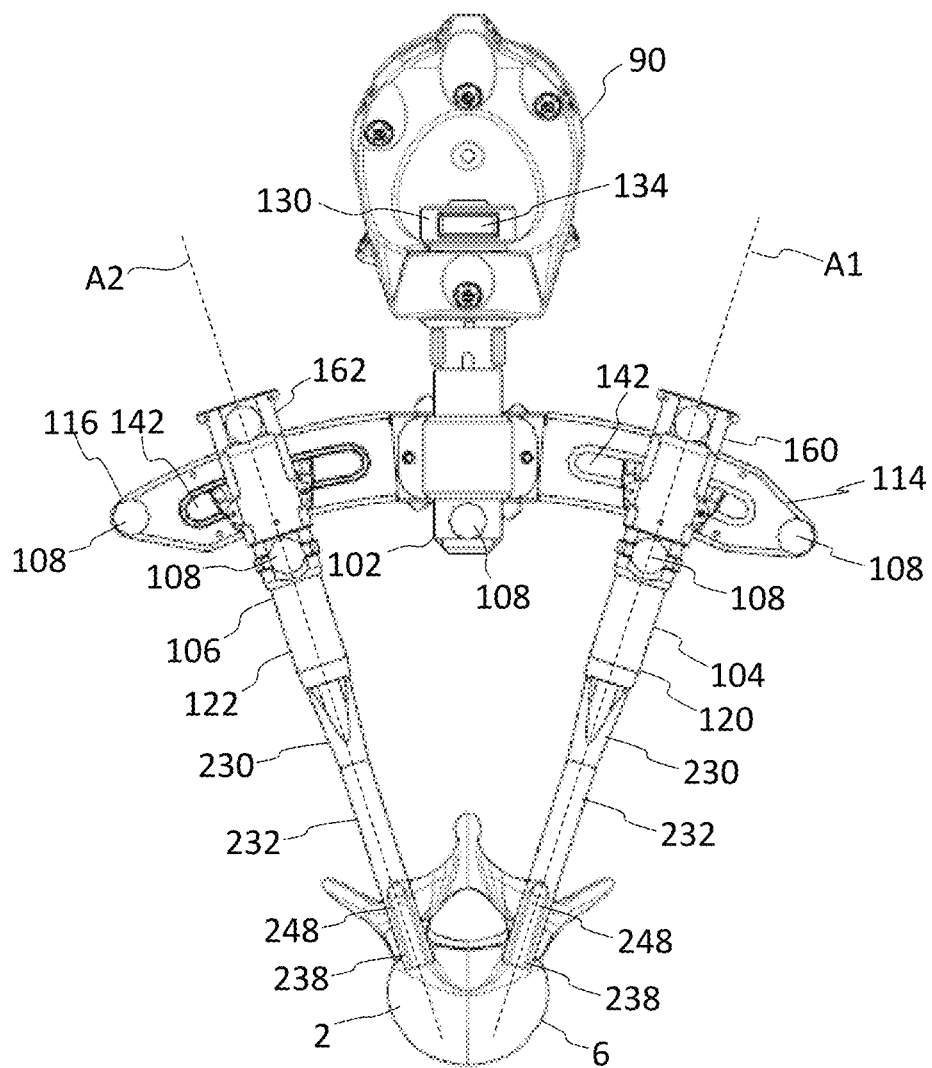
FIGS. 16A-16B show the bi-portal assembly with the adjustable implant cannulas and the cannula dilators, respectively, according to one embodiment.
Figure 16B:
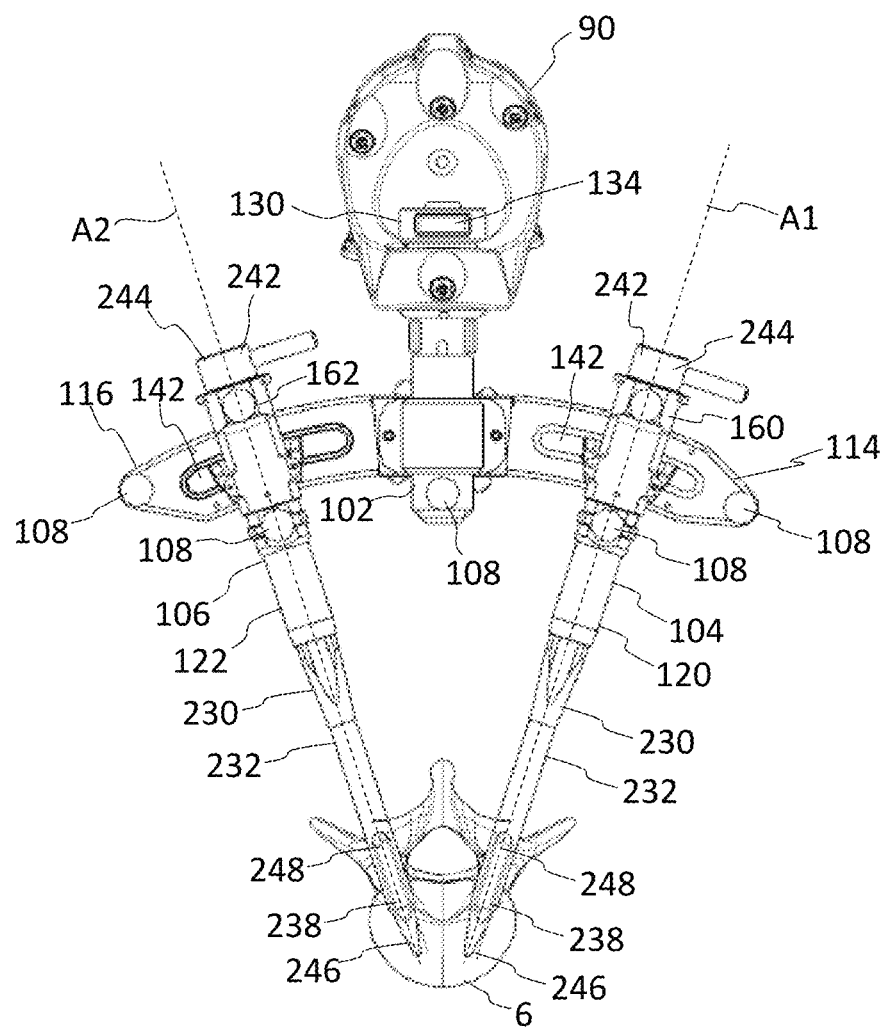

As shown in FIG. 16A, the adjustable implant cannulas 230 may be positioned through the navigation cannulas 120, 122. In FIG. 16B, each cannula dilator 242 is positioned through the implant cannula 230. To assemble, the cap 244 of the dilator 242 may be impacted until the cap 244 hits the face of the navigation cannula 120, 122 and the implant cannula 230 may simultaneously lock into the navigation cannula 120, 122 at the planned depth. The dilators 242 may then be expanded to create or enlarge a space in the bone. After the dilators 242 are removed, the implant cannulas 230 may be used for the discectomy.

Figure 17A:
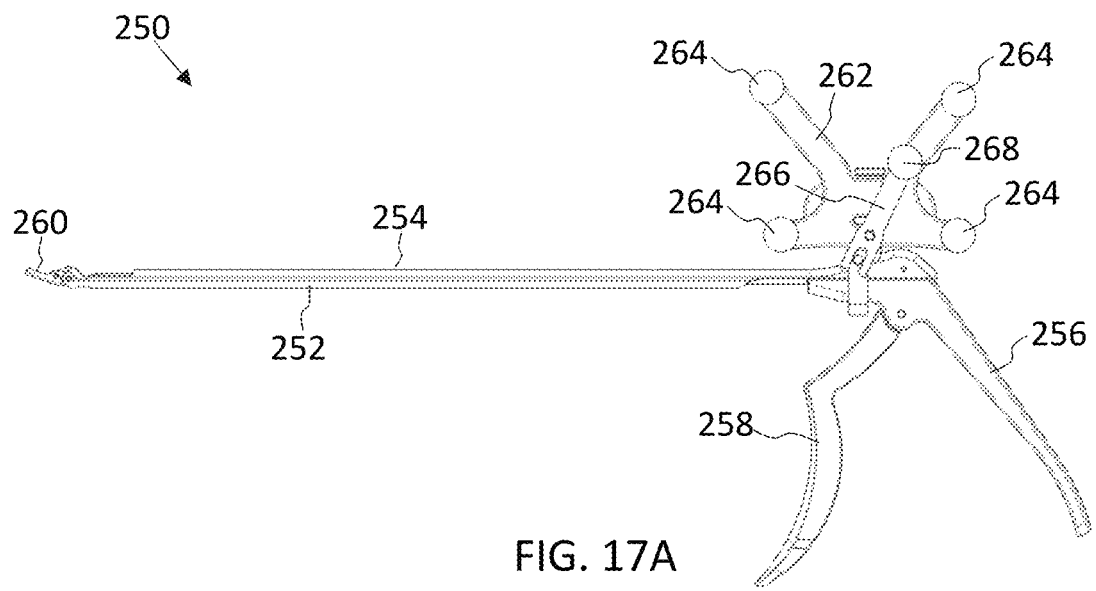
FIGS. 17A-17B show a navigated discectomy instrument according to one embodiment.
Figure 17B:
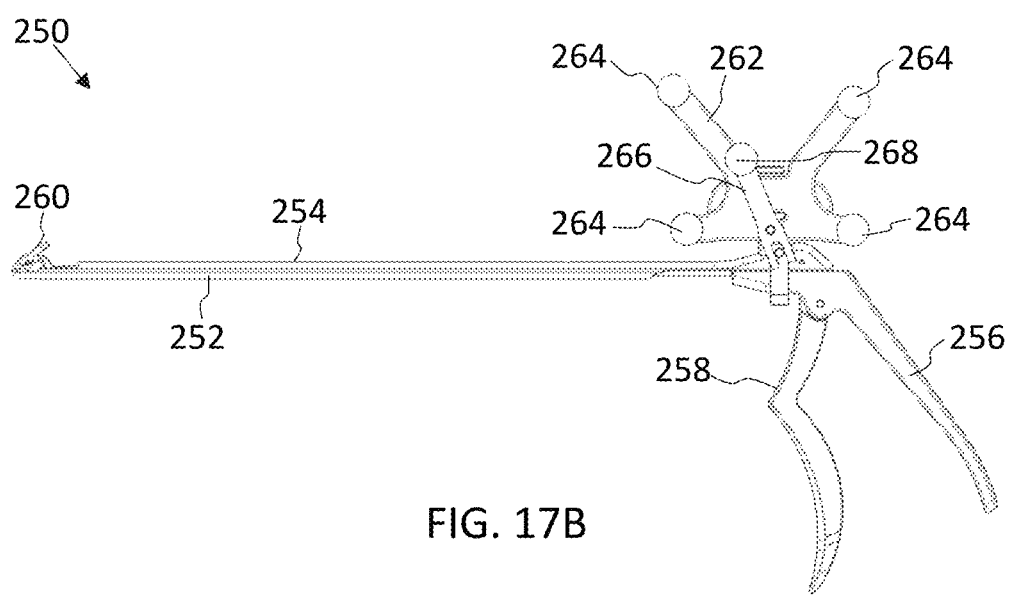

Turning now to FIGS. 17A-17B, a navigatable discectomy instrument 250 is shown according to one embodiment. The navigatable discectomy instrument 250 includes an elongate stationary body 252, an elongate slidable body 254 abutting the stationary body 252, a stationary handle 256 connected to the stationary body 252, an articulating grip 258 pinned to the stationary handle 256, and an articulating distal tip 260 configured to cut bone. When the articulating grip 258 is squeezed toward the stationary handle 256, the slidable body 254 translates longitudinally along the stationary body 252 to thereby pivot the articulating tip 260 about a pivot pin. FIG. 17A shows the articulating tip 260 in an open extended position and FIG. 17B shows the articulating grip 258 squeezed inwardly to pivot the tip 260, thereby folding the tip 260 toward the stationary body 252 to cut and remove soft tissue.

The navigatable discectomy instrument 250 may include one or more tracking markers 264, 268 to track the placement and orientation of the instrument 250 and the articulation of the discectomy tip 260. The stationary body 252 may support a tracking array 262 with a plurality of tracking markers 264, such as spherical passive markers, identified and monitored by the navigation and robotic system 80. In addition, a pivotable arm 266 may support a single marker 268, which moves when the articulating grip 258 is squeezed. The single marker 268 is thus moveable relative to the array 262 of stationary markers 264. As shown in FIG. 17A, the single marker 268 has a first position pointing proximally when the articulating tip 260 is extended distally. When the grip 258 is squeezed and the tip 260 is pivoted, the single marker 268 pivots to a second position pointing distally as shown in FIG. 17B. In this manner, the navigation and robotic system 80 is able to track placement and articulation of the distal tip 260 to confirm soft tissue removal and endplate preparation. This may be used to enhance the discectomy by helping confirm placement and orientation.

Figure 18A:
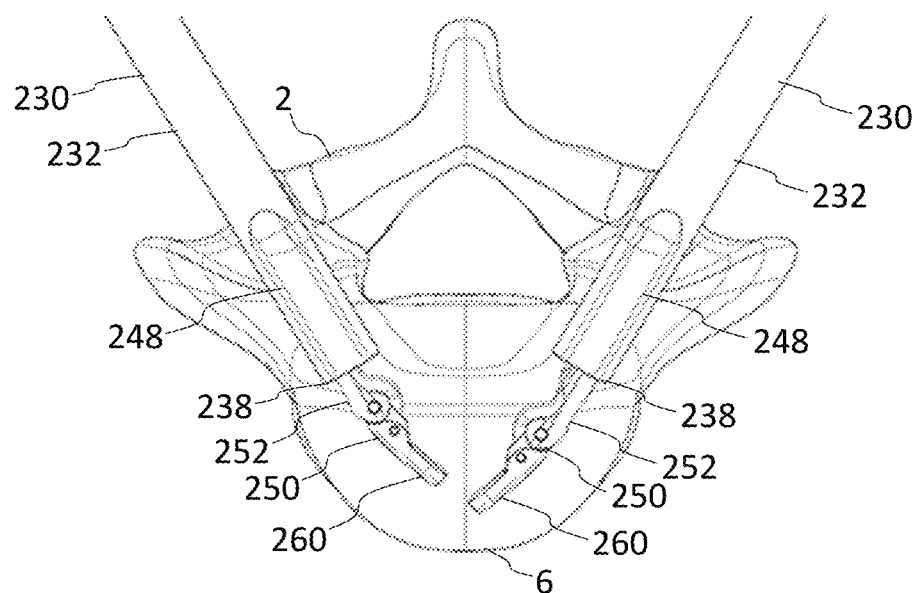
FIGS. 18A-18C show a navigated discectomy procedure through the bi-portal assembly with the adjustable implant cannulas according to one embodiment.
Figure 18B:
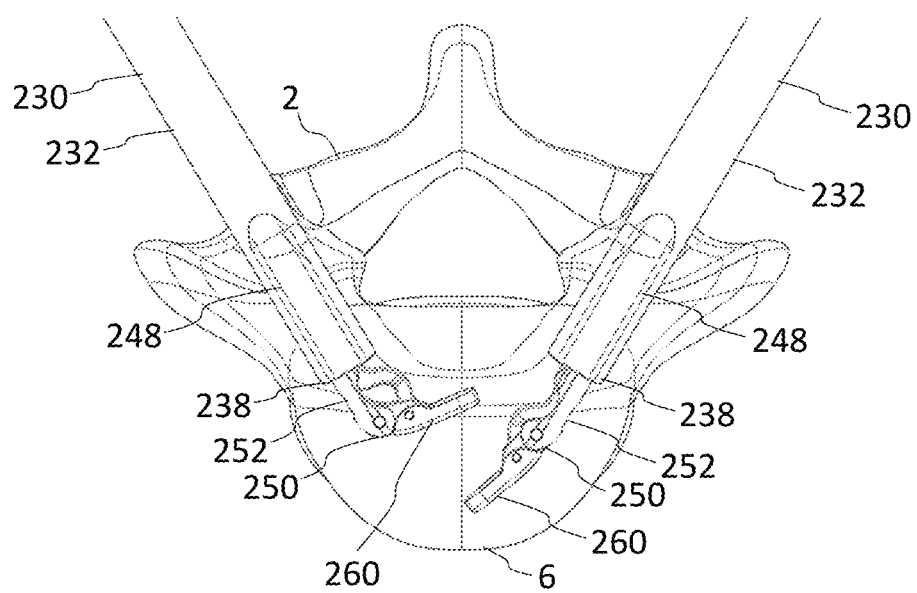
Figure 18C:
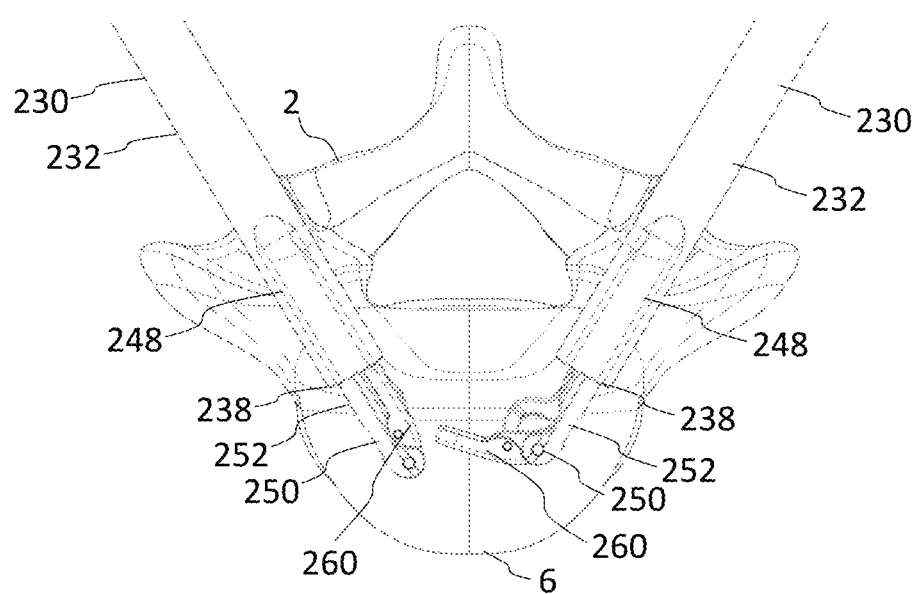

As shown in FIGS. 18A-18C, a discectomy may be performed with the discectomy instrument 250. After the implant cannulas 230 are inserted and locked axially in the navigated cannulas 120, 122, a discectomy may be performed through both implant cannulas 230 to increase the efficiency and overall quality of soft tissue removal. In FIGS. 18A-18C, a pair of discectomy instruments 250 are inserted through the implant cannulas 230 and into the disc space 4 and the articulating tips 260 are pivoted to remove soft tissue. The dual discectomy may lead to easier interbody insertion and positioning, and may increase the volume of bone graft in the disc space to promote faster fusion. The discectomy instrumentation 250 may utilize navigation to track placement and articulation at the distal tip 260 to confirm soft tissue removal and endplate prep in auto-generated volumetric space of the disc.

Figure 19A:
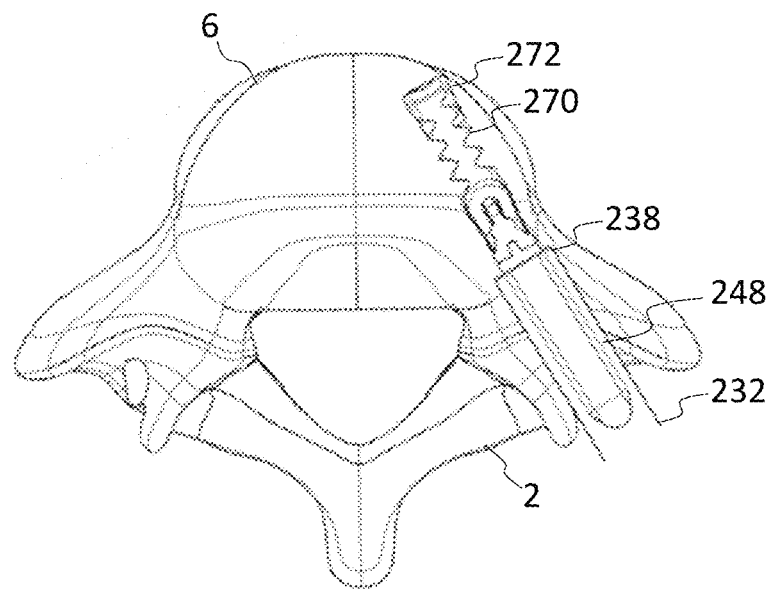
FIGS. 19A-19B show a discectomy procedure with a powered discectomy instrument according to another embodiment.
Figure 19B:
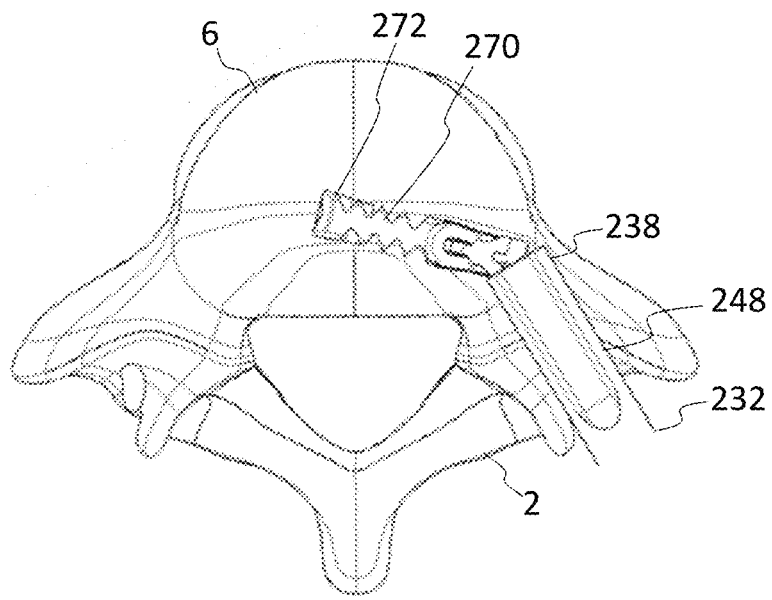

With emphasis on FIGS. 19A-19B and 20A-20C, a powered discectomy instrument 270 is shown according to another embodiment. The discectomy instrument 270 may be powered, for example, by a motor, to provide for enhanced removal of disc material between the endplates of adjacent vertebrae. The powered discectomy instrument 270 may include an articulating soft tissue cutter, curette, or cutting tip 272 that may be configured to release both the nucleus pulpous and annulus fibrosus from the inferior and superior endplates of the vertebrae 2 simultaneously. As shown in FIGS. 19A-19B, the discectomy instrument 270 including cutting tip 272 is configured to fit through the implant cannulas 230 to access the disc space 4. The cutting tip 272 may be articulated to reach around the disc space 4. Although only one implant cannula 230 and instrument 270 is shown, it will be appreciated that the instrument 270 may be used on the contralateral side alone or simultaneously with the ipsilateral side for a bi-portal discectomy.

Figure 20A:
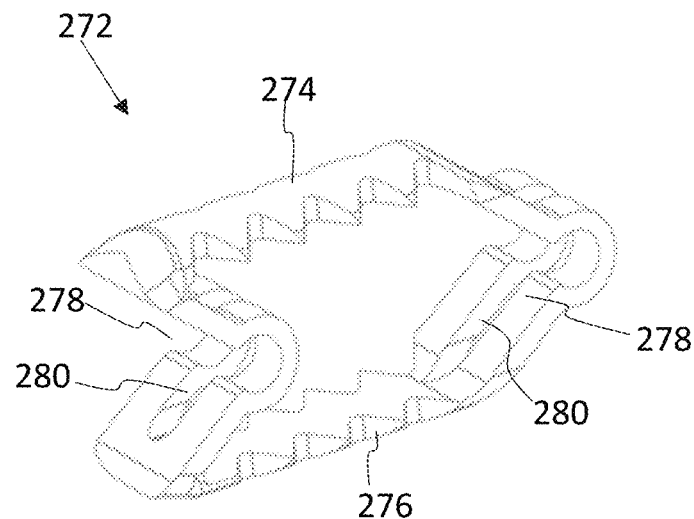
FIGS. 20A-20C show perspective, side, and front views, respectively, of a tissue cutter for the powered discectomy instrument according to one embodiment.
Figure 20B:
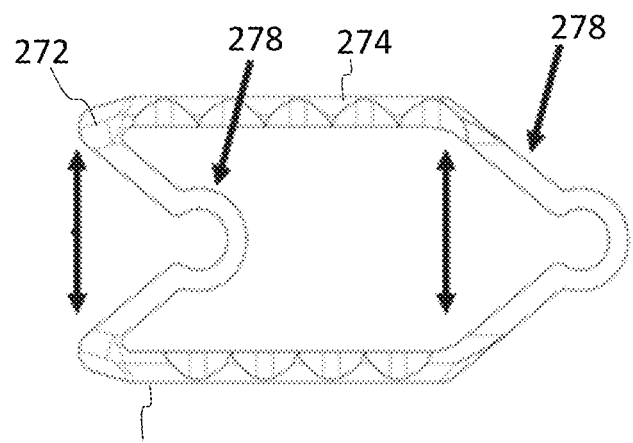
Figure 20C:
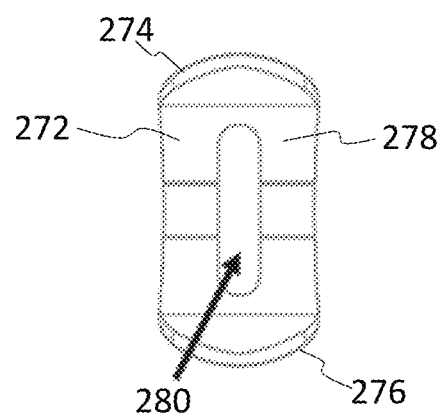

As shown in FIGS. 20A-20C, the cutting tip 272 may include upper and lower endplates 274, 276 with a plurality of teeth configured to cut and release disc material. The cutting tip 272 of the discectomy instrument 270 may be configured for passive expandability. The upper and lower endplates 274, 276 may be able to expand away from one another. As the disc material is cut, released, and evacuated, space is created between inferior and superior endplates of the vertebrae 2. One or more spring cuts 278 in the cutter 272 may allow for the passive expansion. As best seen in FIG. 20C, the spring cut 278 may be bifurcated by a central slit 280, which provides built in clearance for the cutter 272 in its collapsed state.

Turning now to FIGS. 21A-21F, a method of inserting and positioning the expandable interbody implant 12 is shown according to one embodiment. The interbody implant 12 may be positioned into the disc space 4 with a first inserter 300 by inserting the interbody 12 through one implant cannula 230, using a cable 296 to fish the lateral leg 20 of the implant 12 to the opposite implant cannula 230, and connecting the second inserter 302 through the opposite implant cannula 230. A cable assembly 292 threaded onto one leg 20 of the implant 12 may use a magnet 294 to pull the interbody 12 into its natural U-shaped position with the proximal ends of the lateral legs 20, 22 connected to inserters 300, 302 through the respective implant cannulas 230.

Figure 21A:
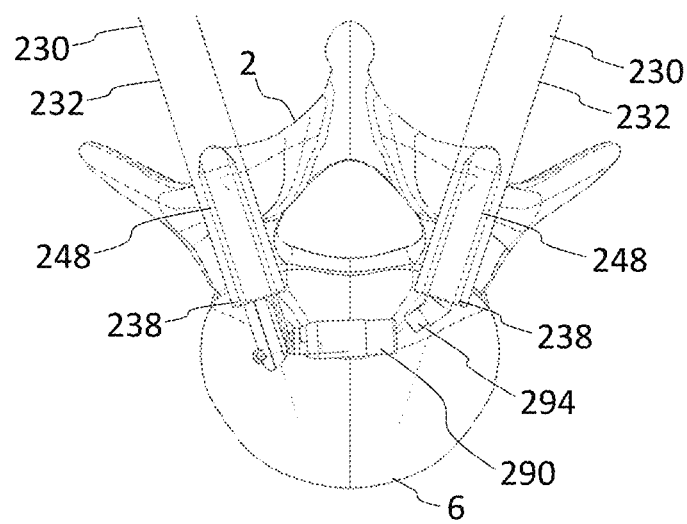
FIGS. 21A-21F show a method of installing the articulating expandable implant of FIGS. 2A-2D in a disc space with a magnetic retrieval and deployment tool and a fishing cable assembly according to one embodiment.

With emphasis on FIG. 21A, an articulated magnet retrieval and deployment tool 290 may be deployed through the contralateral implant cannula 230. The articulated magnet tool 290 may be articulated to guide the tool 290 toward the ipsilateral implant cannula 230. The articulated magnet tool 290 may magnetically attract and connect to a magnetic tip 294 of the cable assembly 292 positioned through the ipsilateral implant cannula 230. The cable assembly 292 includes the magnetic tip 294 attached to a fishing cable 296. The fishing cable 296 may include a cable, wire, rope, chain, or other suitable line configured to be fished between the implant cannulas 230. The fishing cable 296 may have a crimped end at the magnetic tip 294. The opposite end of the fishing cable 296 may be coupled to the end of the lateral leg 20 of the implant 12. For example, the fishing cable 296 may be secured to the implant 12 with a proximal threaded cap 298.

Figure 21B:
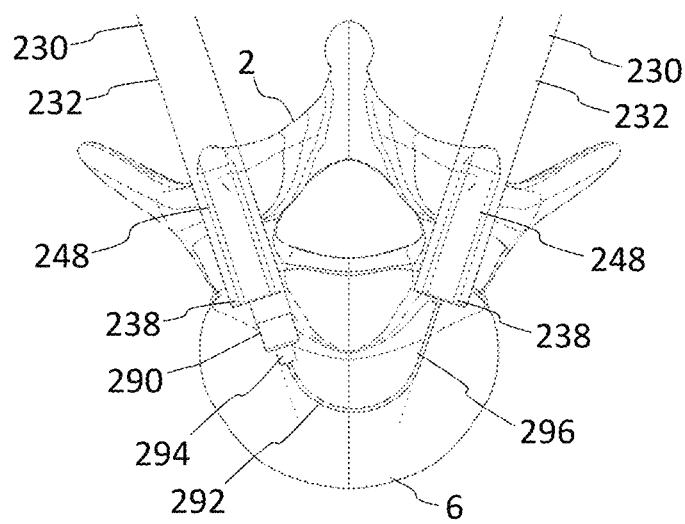

As shown in FIG. 21B, the articulated magnet tool 290 is retracted back through the contralateral implant cannula 230, thereby pulling the magnetic tip 294 and attached cable 296 into the contralateral implant cannula 230. After articulating the magnet retrieval tool 290 to connect and pull the crimped end of the cable assembly 292 through the contralateral implant cannula 230, the cable 296 may be placed under tension as an ipsilateral inserter instrument 300 is rigidly connected to the second lateral leg 22 of the implant 12.

Figure 21C:
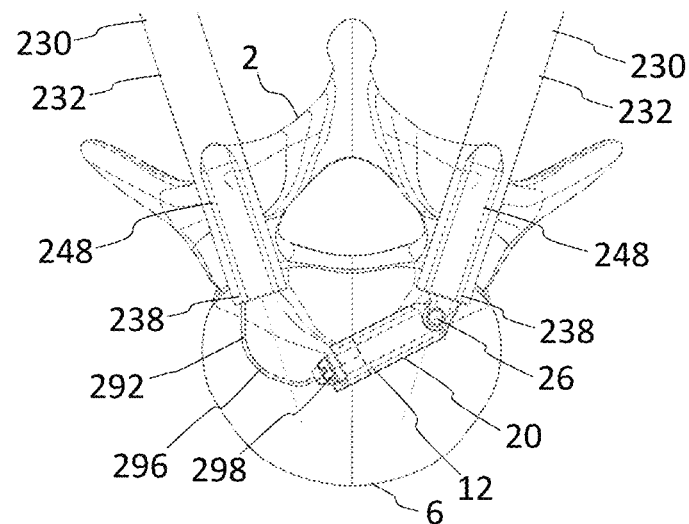
Figure 21D:
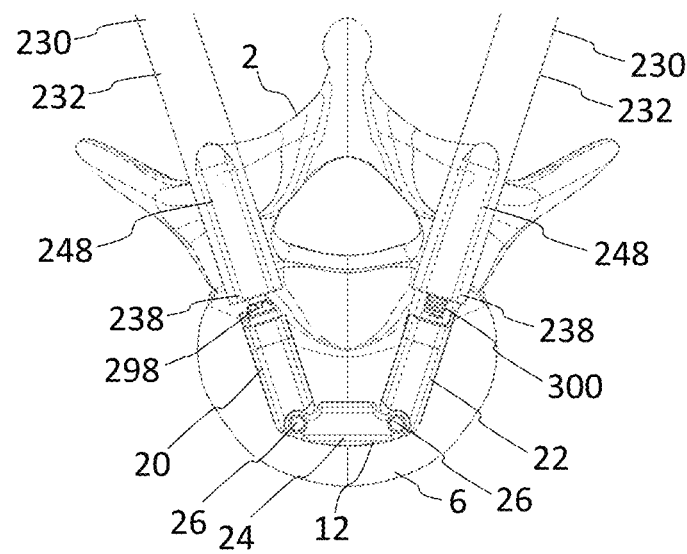

In FIG. 21C, the implant 12 is fed through the ipsilateral implant cannula 230 via inserter 300 with the cable assembly 292 still attached to the opposite end of the implant. 20. The implant 12 articulates at pins 26. As shown in FIG. 21D, the cable 296 may help to pull the interbody 12 into its articulated U-shaped position with the lateral legs 20, 22 bent at pins 26 to increase the overall width or footprint of the implant 12. The threaded cap 298 may be aligned to the outlet of the contralateral implant cannula 230. It may be desirable to check the rigidity of inserter connection before unthreading proximal threaded cap 298 from the interbody 12 to release the cable assembly from interbody 12.

Figure 21E:
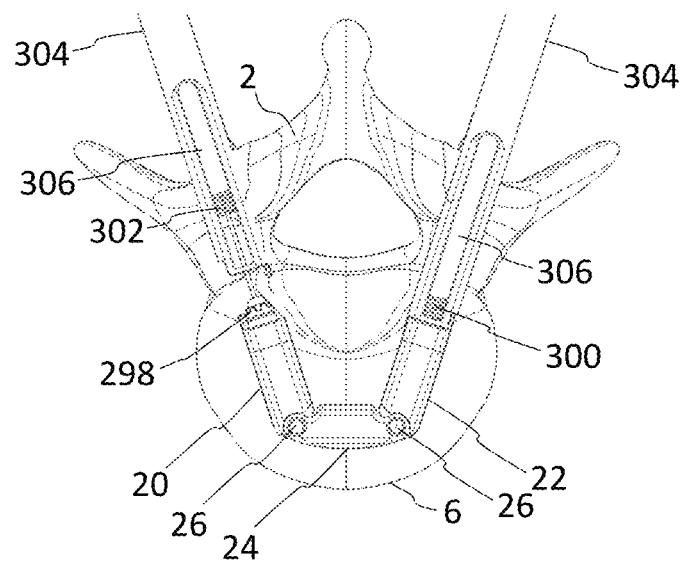
Figure 21F:
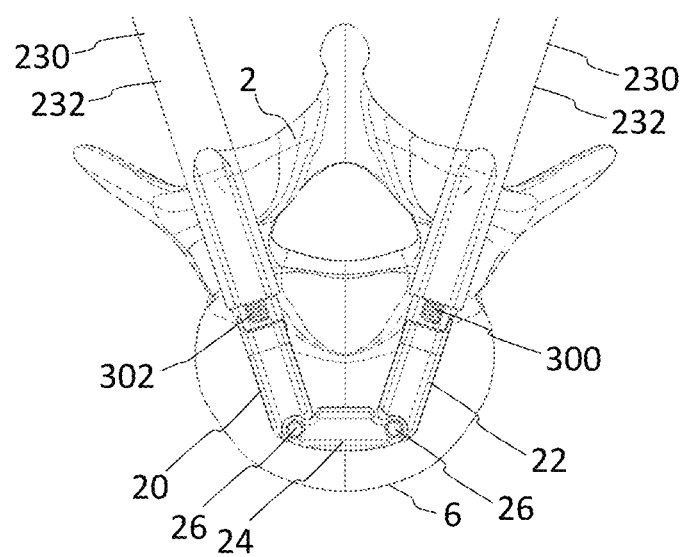

FIG. 21E shows a view of the inserters 300, 302 with the cannulas 230 omitted for clarity. The inserters 300, 302 may each include an outer sleeve 304 with a shaft 306 extending therethrough. The terminal end of the shaft 306 may provide for threaded engagement with the end of the lateral leg 20, 22 of the implant 12. In FIG. 21E, the threaded sleeve 304 and counter torque shaft 306 of the second inserter instrument 302 is positioned through the contralateral implant cannula 230. In the final configuration shown in FIG. 21F, the second inserter 302 is threaded onto the contralateral leg 20 of the implant 20 while the first inserter 300 is still rigidly connected to the ipsilateral leg 22 of the implant 20. This dual connection provides for dual interbody control of the implant 12. Thus, the overall position of the implant 12 and each of the lateral legs 20, 22 may be manipulated or moved by both inserters 300, 302.

Figure 22:
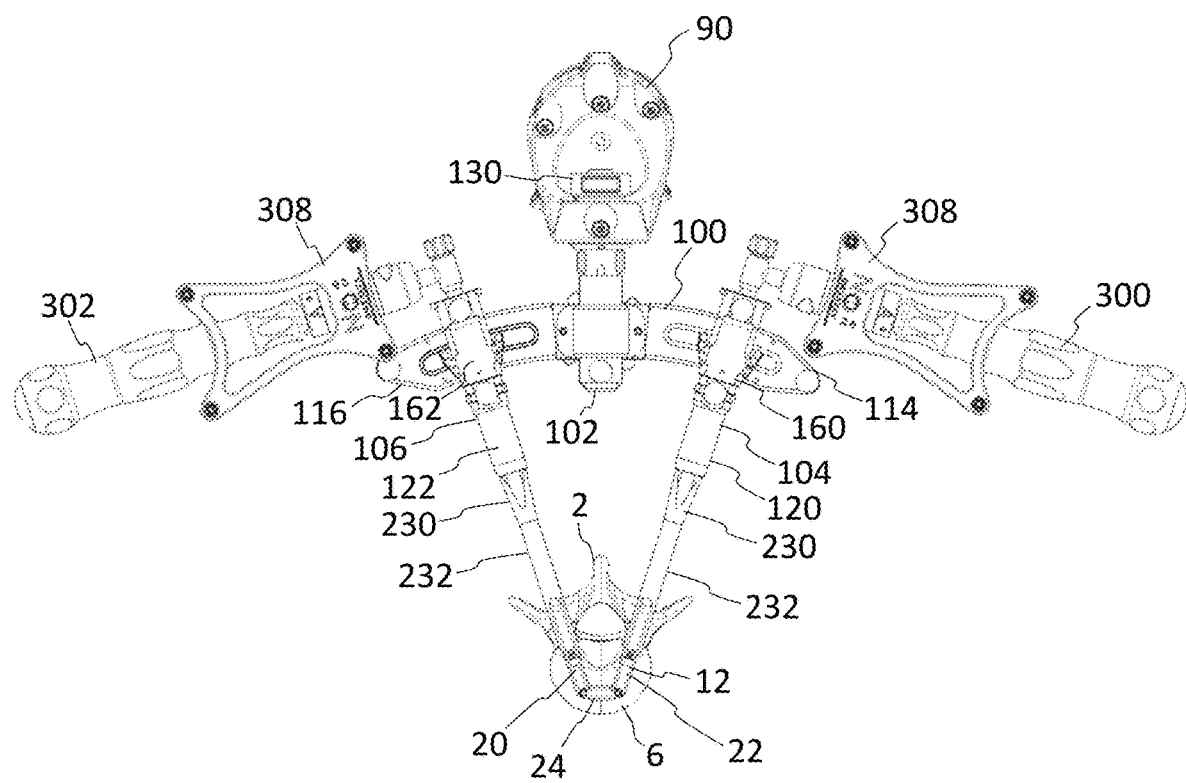
FIG. 22 shows a complete overview of the bi-portal assembly with navigable inserters positioned through the ipsilateral and contralateral implant cannulas according to one embodiment.

FIG. 22 shows a complete overview of the bi-portal assembly 100 with both navigable inserters 300, 302. The guide bar assembly 102 secures the first and second navigated cannula assemblies 104, 106 along the desired trajectories. The implant cannulas 230 are positioned through the respective navigated cannula assemblies 104, 106. The inserters 300, 302 are positioned through the respective implant cannulas 230. Once both inserters 300, 302 are connected to the lateral legs 20, 22 of the implant 12, navigable arrays 308 may be attached to the inserters 300, 302 for precise placement of the interbody 12, thereby providing for superior segmental correction and stabilization.

Figure 23A:
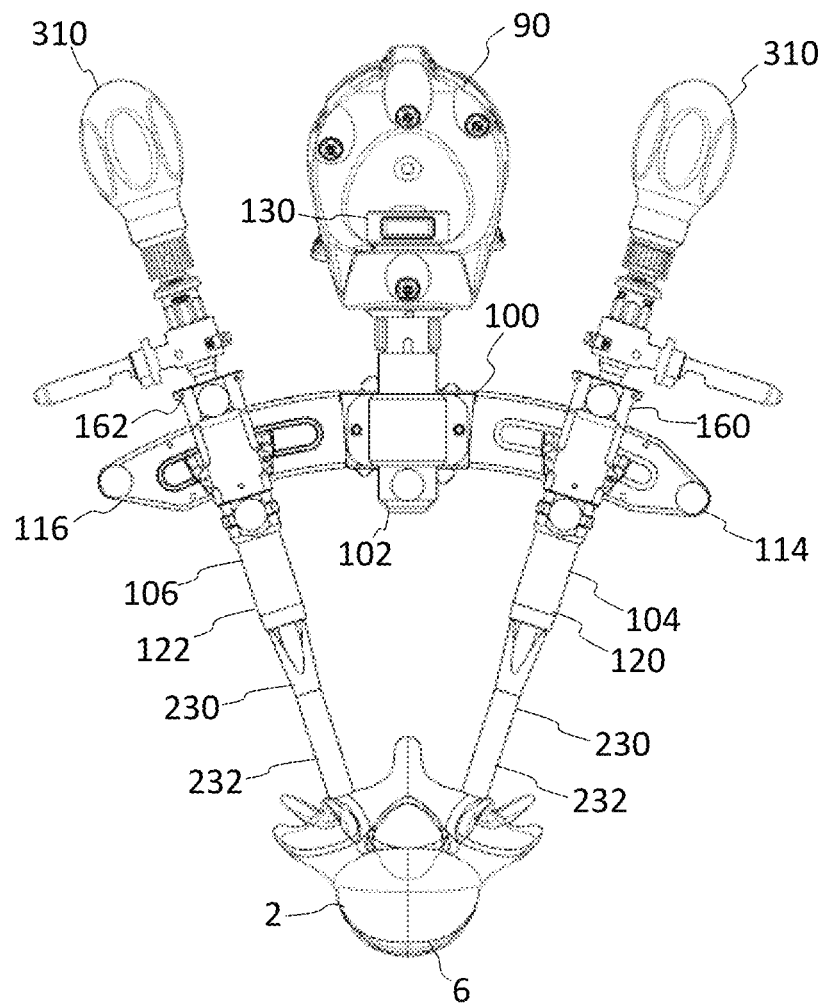
FIGS. 23A-23B show front and perspective views, respectively, of the bi-portal assembly with ipsilateral and contralateral inserters snap fit to the respective inserters according to one embodiment.
Figure 23B:
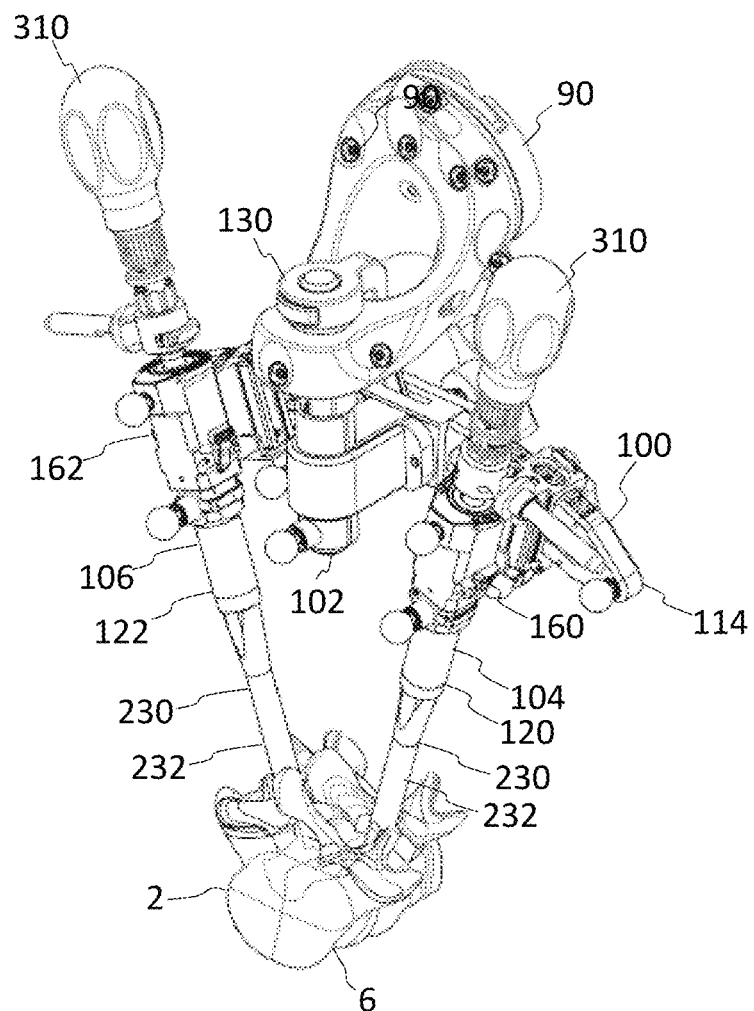

Turning now to FIG. 23A-23B, once the collapsed interbody implant 12 is accurately placed and positioned, drivers 310 may be placed through the inserters 300, 302 to expand the implant 12. After the handle and array 308 of the inserter 300, 302 is removed, the drivers 310 may be placed down both the ipsilateral and contralateral inserters 300, 302 and clipped in axially to the respective inserters 300, 302. The distal tip of each driver 310 may interface with the actuation members 30 of the implant 12 to allow for independent expansion of the lateral legs 20, 22 of the implant 12. The handle of the driver 310 may be rotated to rotate the actuation member 30, thereby expanding the respective leg 20, 22 of the implant 12. Arrays and/or smart instrumentation may be utilized to ensure parallel, lordotic, coronal, or other desired expansion for the implant 12.

Figure 24A:
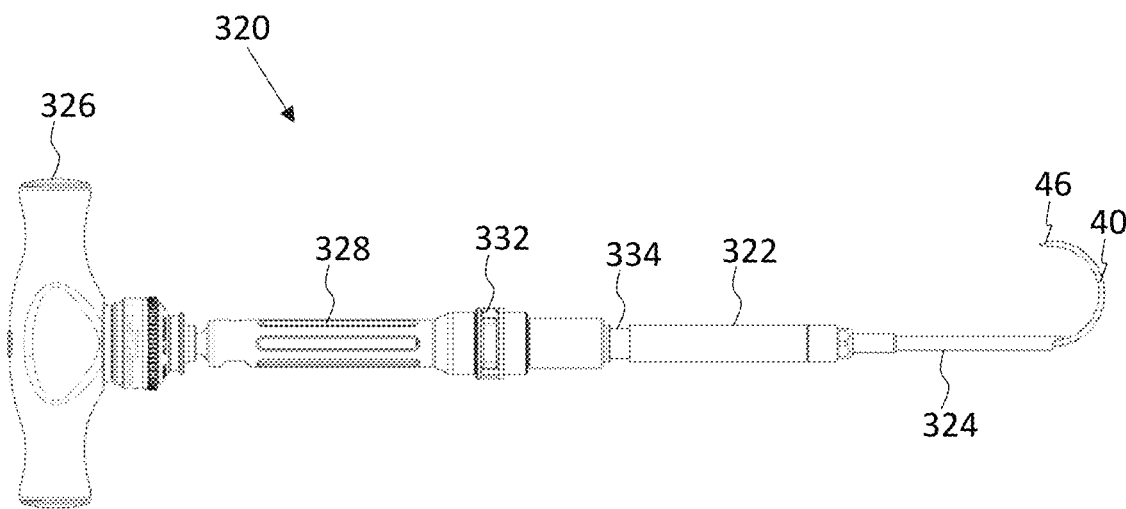
FIGS. 24A-24C show a nitinol rod fixation instrument configured for loading and deploying the nitinol rod of the pedicle-based intradiscal fixation implant shown in FIGS. 3 and 4A-4B.
Figure 24B:
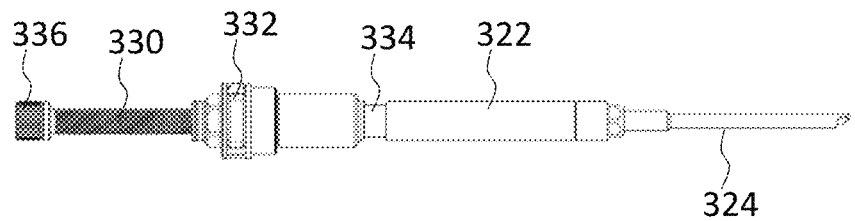
Figure 24C:
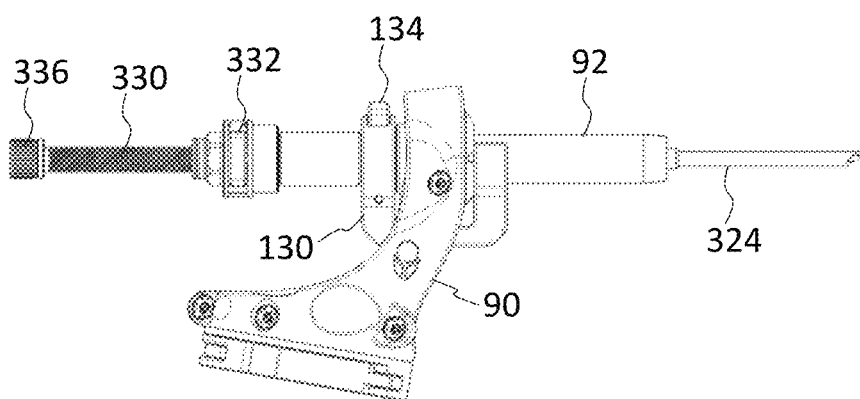

Turning now to FIGS. 24A-24C and 25A-25F, after the interbody 12 is implanted, the pedicle-based intradiscal fixation implants 14 may be installed. FIGS. 24A-24C show a rod fixation instrument 320 according to one embodiment. The rod fixation instrument 320 is configured to load and deploy the rod 40 of the pedicle-based intradiscal fixation implant 14. The rod fixation instrument 320 may include a body 322 with a deployment tube 324 at its distal end. The deployment tube 324 is straight and configured to draw in the curved rod 40, thereby straightening the rod 40 when held within the deployment tube 324. The instrument 320 may load the nitinol rod 40 into the straight deployment tube 324 by drawing the rod 40 in from the threaded proximal end 48. The deployment tube 324 may be customized for specific size offerings as the bend diameter, or cephalad-caudal height, of the nitinol rod 40 may have a proportional rod thickness to improve super elastic properties in proportion to its strength.

The rod fixation instrument 320 may include a T-shaped handle 326 with a socket 328 configured to be received over a shaft 330 with an impaction cap 336. The socket 328 snaps in drive engagement with button 332. When the handle 326 is rotated about the longitudinal axis of the instrument 320, the nitinol rod 40 is drawn into the deployment tube 324. The handle 326 may be released by snap release of the drive engagement button 332. As shown in FIG. 24C, after the guide bar assembly 102 has been removed from the guide tube 92 of the end-effector 90, the nitinol deployment instrument 320 is subsequently positioned through the guide tube 92 of the end-effector 90. The instrument 320 may be locked into the axial locking cap 130 by an outer circumferential groove 334 in the body 322 of the instrument 320.

Figure 25A:
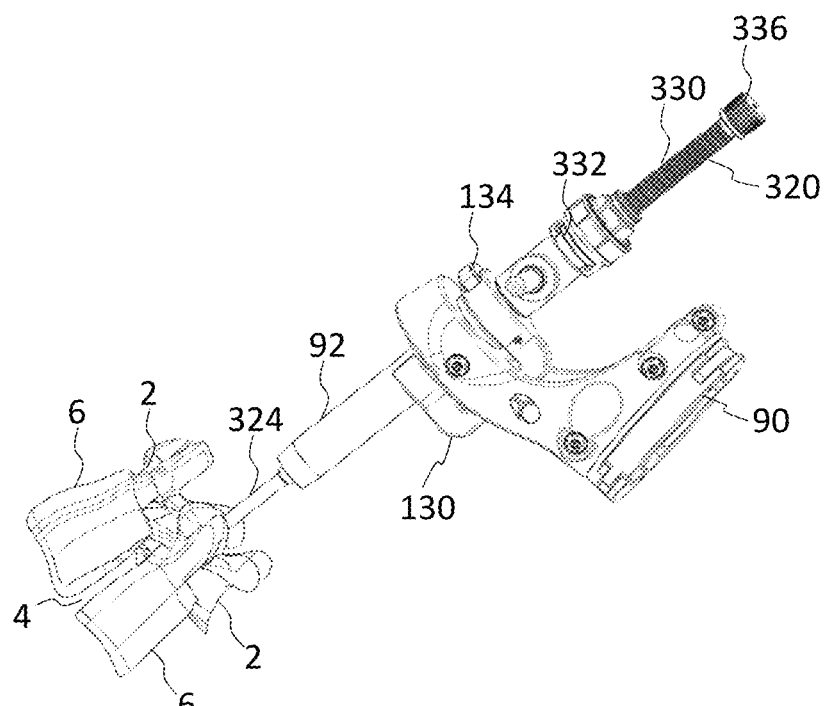
FIGS. 25A-25F show a system and method for deploying the nitinol fixation rod and attaching the pedicle screw to the rod according to one embodiment.
Figure 25B:
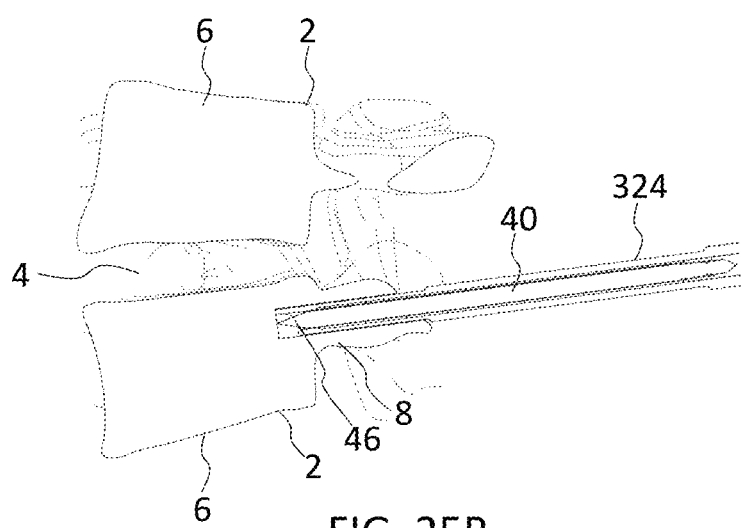

As shown in FIGS. 25A-25B, the rod fixation instrument 320 is set into position for deploying the rod 40. The end-effector 90 is set in position after the posterior of the spine is accessed. A hole may be pre-drilled into the pedicle 8 of the inferior vertebra 2. The nitinol rod 40 may be set into the prepped hole, locked into the end-effector 90, and ready for impaction for deployment.

Figure 25C:
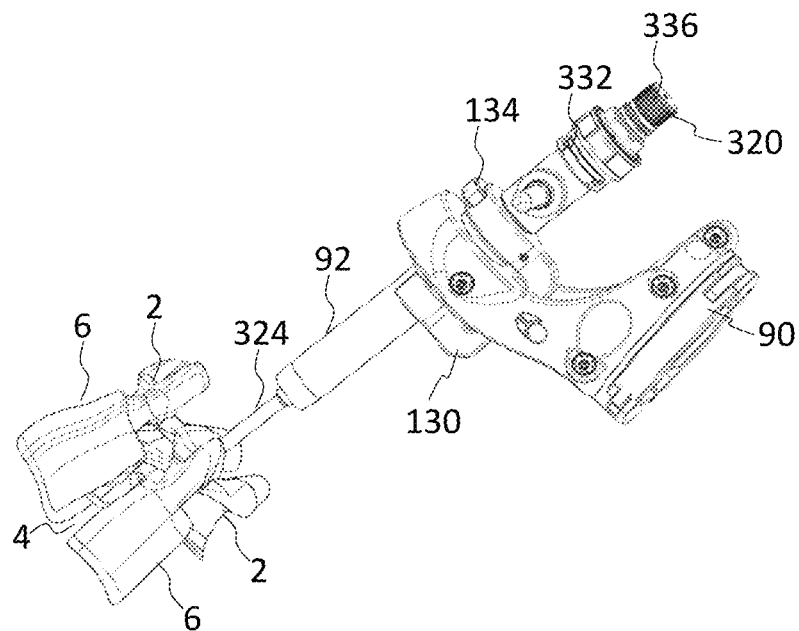
Figure 25D:
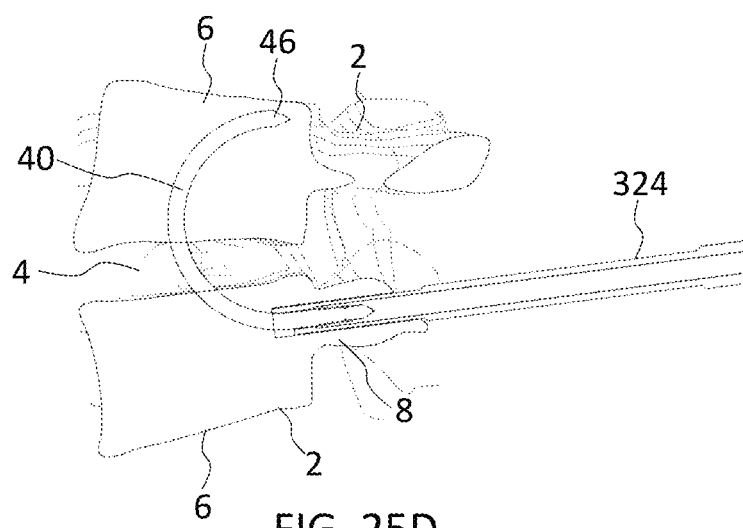

In FIGS. 25C-25D, the nitinol rod 40 is deployed through the inferior vertebral body 6, through the disc space 4, and into the superior vertebral body 6. The shaft 330 of the deployment instrument 320 may be translated distally along the longitudinal axis of the instrument 320, for example, by striking the impaction cap 336 with a surgical mallet. The shaft 330 forces the nitinol rod 40 to deploy out of the deployment tube 324. The properties of super elastic nitinol allow for the nitinol rod 40 to return to its natural, curved state throughout the deployment process, sweeping from the inferior pedicle 8, thru the intradiscal space 4, medially to the lateral interbody legs 20, 22, and into the superior vertebral body 6. After the impaction cap 336 bottoms-out, the rod 40 is fully deployed, and the deployment instrumentation 320 may be removed.

Figure 25E:
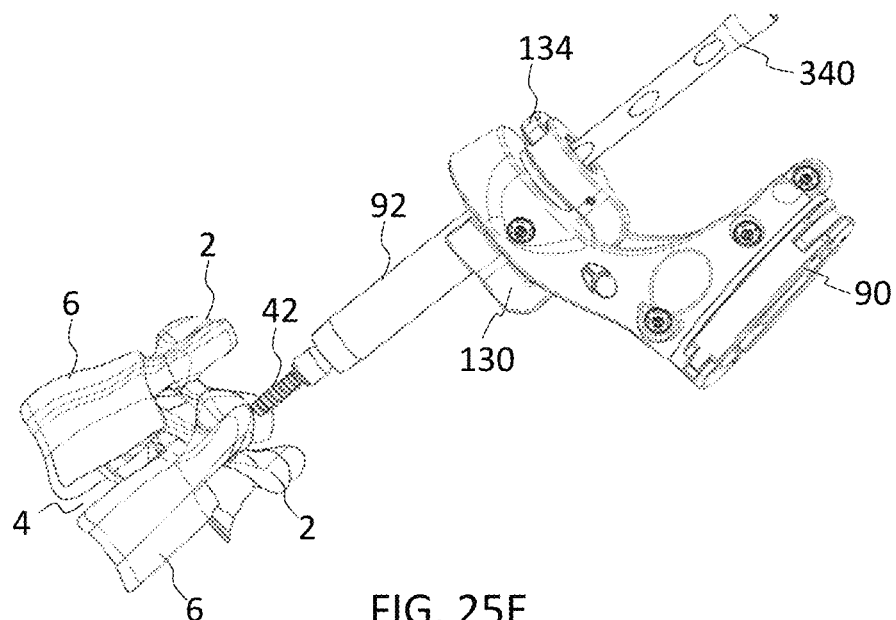
Figure 25F:
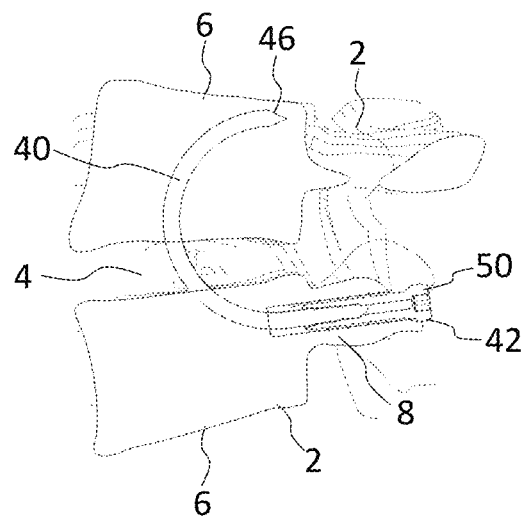

In FIGS. 25E-25F, the pedicle screw 42 is secured and anchored to the nitinol rod 40. A driver 340 positioned through guide tube 92 inserts the pedicle screw into the inferior pedicle 8. The pedicle screw 42 is inserted and driven over the proximal threads 48 of the nitinol rod 40 to purchase the existing cortical bone in the pedicle 8 and anchor the proximal end 44 of the nitinol rod 40 to the inferior pedicle 8. The process shown in FIGS. 25A-25F may then be repeated for the second intradiscal fixation implant 14 on the contralateral side.

Figure 26A:
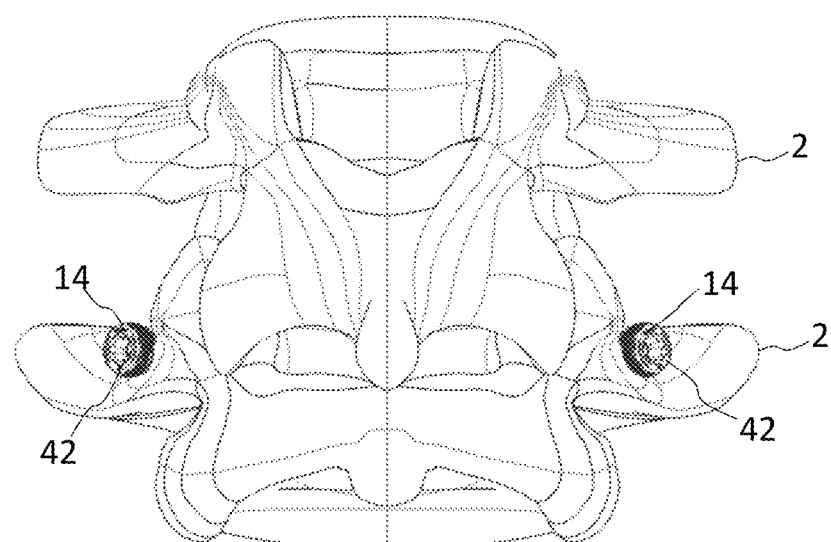
FIGS. 26A-26D show posterior, lateral, anterior, and intradiscal views, respectively, of the final construct including the expandable interbody implant and two intradiscal fixation devices according to one embodiment.
Figure 26B:
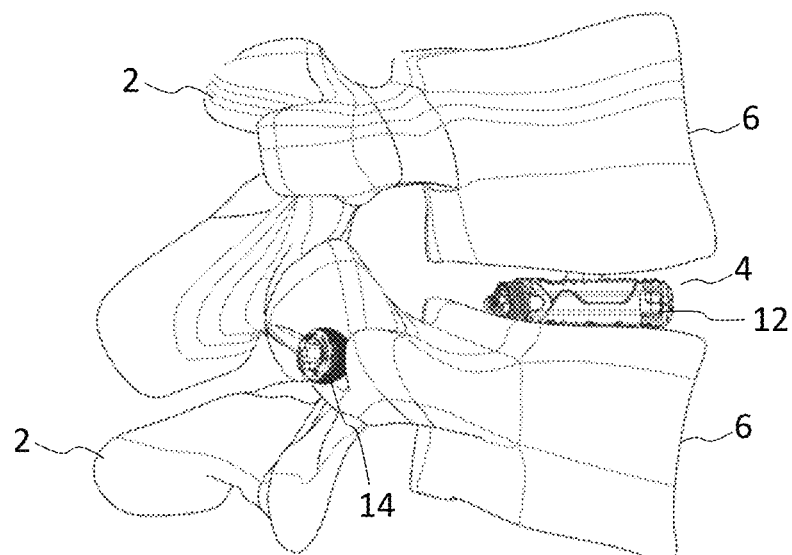
Figure 26C:
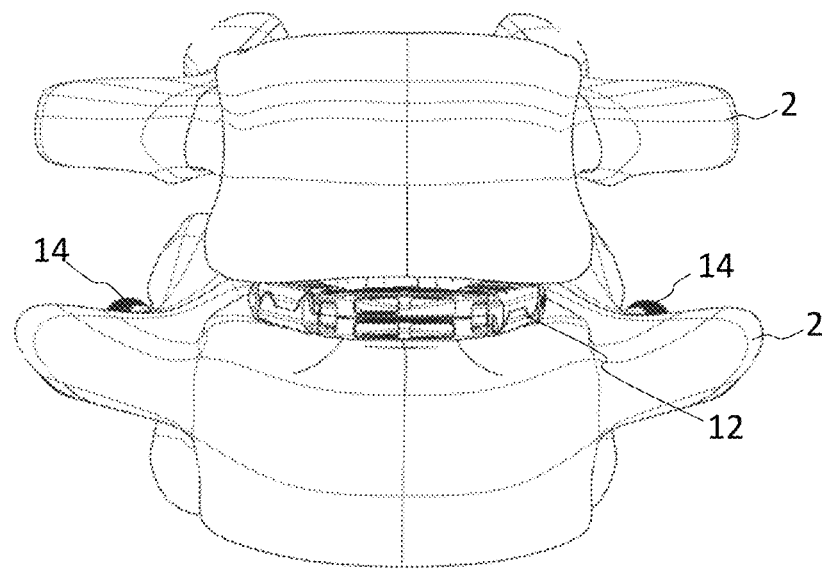
Figure 26D:
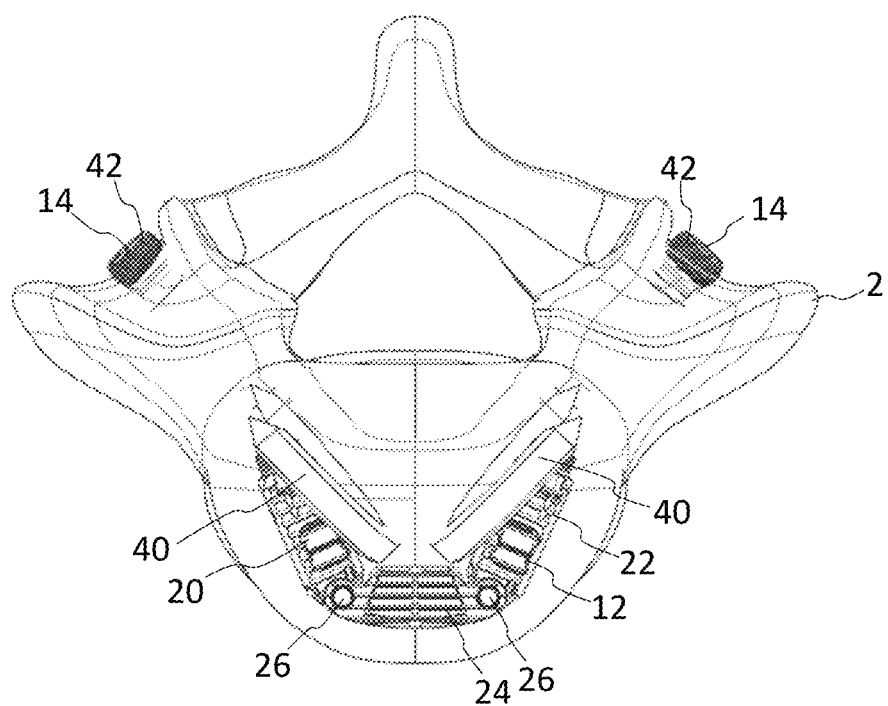

FIGS. 26A-26D show an example of the completed construct 10 including the interbody implant 12 and two intradiscal implants 14. FIG. 26A provides a posterior view of the spine and the two intradiscal implants 14 positioned into the pedicles 8 of the inferior vertebra 2. FIG. 26B shows a lateral view of the spine with the interbody implant 12 positioned in the disc space 4 between the vertebrae 2. FIG. 26C shows an anterior view of the spine and the interbody implant 12. FIG. 26D is an intradiscal view of the system 10 including the interbody implant 12 and two intradiscal implants 14. The completed construct 10 provides superior stabilization from a posterior approach. The intradiscal implants 14 do not violate the superior facet joint, limiting adjacent segment disease that can be a result of superior adjacent facet violation.

According to one embodiment, the procedure may be performed with navigation and/or robotic assistance. The robotically-enabled procedure may include a workflow assisted and enhanced using imaging, navigation and robotics including: (1) pre-operative planning; (2) end-effector set-up; (3) tubular access and decompression or alternative visualization port workflows; (4) bi-portal implant cannula insertion; (5) bi-portal discectomy; (6) interbody deployment, positioning, and expansion; (7) nitinol fixation construction; and (8) final verification. The robotically-enabled procedure may utilize imaging, navigation, and robotics to enhance the quality and efficiency of the posterior procedure through planning and navigable instrumentation.

The first step in the workflow may include pre-operative planning. The importance of a structured workflow for the robotically-enabled bi-portal interbody fusion technique is stressed in pre-operative imaging and planning stages. A step-by-step user interface may be provided on the monitor 88 of the robot 80 to walk healthcare professionals through precise interbody placement, depth-controlled access-decompression instrumentation, and fixation planned deployment. The control of these aspects may be enhanced with sagittal, axial, coronal, and 3D volumetric views of patient anatomy with the addition of CT-MRI merge displays to recognize and visualize neural elements for safe and repeatable procedures.

The planning stage may follow a detailed checklist. After selecting the level to be corrected on the monitor 88, a virtual representation of the anterior or center leg 24 of the 3-legged interbody implant 12 may be placed along the anterior side of the apophyseal ring on midline. This interbody 12 has dual, independent expansion and angulation on the lateral legs 20, 22. The interbody 12 may utilize bi-portal access into the disc space 4 based of the width of the anterior leg 24 and angulation and length of the lateral legs 20, 22. Angulation of lateral legs 20, 22 may be controlled on the transverse plane on the planned level, shifting from medial to lateral. Parallel and lordotic expansion of the lateral legs 20, 22 may be planned prior to the procedure either independently or mirrored to one another. All sizing, positioning, and expansion of the interbody footprint are to help customize the correction to patient anatomy.

Once the planned anterior width and leg angulation are set, a surgeon may plan for the removal of posterior bone anatomy to gain access into the disc space 4. For example, pre-planned depth stops may be used for access instrumentation on the given trajectory. In one embodiment, stops 160, 162 may be set to protect neural anatomy from powered instrumentation. The planned implant cannula depth may be set independently in relation to the proximal ends of the left and right lateral legs 20, 22 of the interbody 12.

The final stage in the pre-op planning checklist is to plan the nitinol fixation implants 14 with regards to trajectory, rod sizing, and pedicle screw sizing. The nitinol fixation implant 14 may be set medially to the lateral legs 20, 22 and posteriorly to the anterior leg 24 of the interbody 12. Size offerings are determined based on which bend diameter fits within the inferior and superior vertebral bodies 6 without violating the facet or damaging the axis of the pedicle 8 of the superior vertebra 2. Pedicle screws 42 may be sized to ensure the capture of the proximal end 44 of the nitinol rod 40 with the screw 42 while the screw head 50 is protruding from the pedicle 8.

The second step in the workflow may include end-effector manual set-up. Once the pre-op plan summary is complete, the guide bar assembly 102 may be introduced to the end-effector 90 to introduce single position, bi-portal control. The axial locking cap 130 may be snapped on an inside portion of the end-effector 90 to avoid blocking the infrared LEDs 132. The guide bar 110 may be slid through the inner diameter of the guide tube 92 of the end-effector 90 to lock the assembly axially with the end-effector height. In an alternative design, the connection to the robot 82 could be built into the guide bar 110 rather connecting through the end-effector 90.

Once the guide bar 110 snaps in and locks axially, the assembly 100 may be rotated about the end-effector 90 until the planned levels plane is parallel with the navigated cannulas 120, 122. Markers 108 are identified by the camera system 94 to callout the degrees off the plane, and the guide bar 110 may be final locked when the callout is at 0°. Following rotationally locking the guide bar 110, the width of the guide bar assembly 102 may be manually adjusted to match the anterior legs width and then angles of the navigated cannulas 120, 122 may be adjusted to be consistent with the pre-op plan, sizing, and positioning. Axis of the navigated cannula 120, 122 may line up with the medial-lateral angle of the lateral leg 20, 22 found in the plan summary. The navigated cannulas 120, 122 may be final locked to ensure guide bar and nav cannula rigidity before moving forward to depth control.

Working with an outside-in approach, access-decompression may begin to remove the bilateral facet joints. Safety and protective precautions may be taken for exiting neural elements, for example, by setting the adjustable stop 160, 162 to its initial depth. Depth control may be set according to plan and remains independent on the left and right trajectories for customized access for abnormal patient anatomy. An alternative design to this manual set-up is providing power to a single position, bi-portal end-effector that can auto-generate the width, angulation, and adjustable depth control settings according to the pre-operative plan.

The third step in the workflow may include tubular access and decompression or alternative direct visualization ports. There remains variability in surgeons' comfort with the tubular approach in comparison to direct visualization while removing posterior structural anatomy and protecting neural elements anteriorly to the facet joint. To accommodate, alternative workflow consisting of direct visualization ports 194 can be utilized with the guide bar system 102 in addition to the tubular access and decompression workflow. Hybrid use of high-speed burrs, oscillating drills, and manual osteotome instrumentation may be utilized to enhance comfort for surgeons from different technical backgrounds and training. Alternative workflows keep the same trajectory planned with benefits provided with each workflow.

The MIS access workflow with the navigated cannulas 120, 122 provides tubular access and decompression benefits including: (1) depth control compatibility; (2) navigated cannula compatibility with dilator, off-center sheath, docking facet dilator, and instrumentation; (3) reduced amount of posterior structural anatomy; and (4) streamlined to insert interbody cannula immediately. The direct visualization access workflow with ports 194 may have conical angulation. The direct visualization may provide for increased visualization for thorough decompression and increased visualization may increase safety with regards to neural elements.

The fourth step in the workflow may include bi-portal implant cannula insertion. After a thorough access and decompression have sufficiently removed all obstructing bone from the bilateral trajectories, regardless of access workflow used, navigated cannulas 120, 122 may be used with the adjustable stop 160, 162 locked into its lowest height for implant cannula insertion. Implant cannula 230 may be adjusted to planned depth according to plan, and then cannula dilator 242 may be loaded into the keyed feature 248 at the distal tip 238 of the cannula 232. The proximal end of cannula dilator 242 may be impacted until the cap 242 hits the face of the navigated cannula 120, 122, and implant cannula 230 simultaneously locks into the navigated cannula 120, 122 at the planned depth. The cannula dilator 242 may be removed to begin the discectomy.

The fifth step in the workflow may include the discectomy. Once both implant cannulas 230 are inserted and locked axially, a discectomy may be performed through both implant cannulas 230 to increase the efficiency and overall quality of soft tissue removal. This may lead to easier interbody insertion, positioning and increase the volume of bone graft in the disc space to promote faster fusion. A heat map may be automatically generated based on interbody placement to calculate a volumetric area where tools can and should be placed to remove soft tissue.

Discectomy instrumentation 250 may utilize navigation to track placement and articulation at the distal tip 260 to confirm soft tissue removal and endplate prep in auto-generated volumetric space of the disc. The array sphere 268 may track the mechanical articulation according to the customized array positioning. This may enhance the discectomy by helping confirm placement and orientation. The robot 82 may also read out areas in which a tool path has or has not passed through to ensure sufficient soft tissue removal and surface area of endplates have been prepped.

Bi-portal navigated discectomy may have variability in technique allowing for surgeon preference to select between navigated manual instrumentation 250, powered discectomy instrumentation 270, or a hybrid use of both. Both technique workflows may be completed with manual endplate prep instrumentation to help ensure increased fusion rates and to verify the passing of instrumentation throughout the auto-generated volumetric heat map.

The sixth step in the workflow may include interbody deployment and positioning. After a thorough discectomy is completed, the 3-legged interbody 12 may be positioned by inserting the interbody 12 through the ipsilateral implant cannula 230, using a cable 292 to fish the contralateral lateral leg 20 to the contralateral implant cannula 230, and connecting the second inserter 302 through the contralateral implant cannula 230. Utilizing two hinge pins 26 to connect the three legs 20, 22, 24 and a cable assembly 292 threaded onto the contralateral leg 20, a magnet pulls the interbody 12 into its natural U-shaped position with the proximal ends of the lateral legs 20, 22 connected to inserters 300, 302 through the implant cannula 230.

After articulating the magnet retrieval tool 290 to connect and pull the crimped end of the cable assembly 292 through the contralateral implant cannula 230, the cable 296 may be placed under tension as the contralateral inserter 300 is rigidly connected to the lateral leg 22. Rigidity of inserter connection may be checked before unthreading the proximal threaded cap 298 from the interbody 12 to release the cable assembly 292 from the interbody 12.

Once both inserters 300, 302 are connected to the lateral legs 20, 22, navigable arrays 308 may be attached to the inserters 300, 302 for precise placement of the interbody 12 for superior segmental correction and stabilization. Views from the sagittal, axial, and coronal planes as well as a 3D volumetric view may enhance a surgeon's ability to place the interbody 12 in the planned position with dual inserter control. Trajectories may be locked as a result of the pre-op plan and guide bar set-up, but depth and orientation of the anterior and lateral legs 20, 22 may be confirmed using navigation prior to expansion.

Once the collapsed interbody 12 is accurately placed, drivers 310 may be placed down both the ipsilateral and contralateral inserters 300, 302 and clipped in axially to the respective inserters 300, 302. Arrays and/or smart instrumentation may be utilized to read-out both parallel, followed by lordotic, expansion for both the left and right sides individually. Same as the rest of the procedure, the planned summary may list the expandable implant's target height, lordotic, and coronal correction.

The seventh step in the workflow may include installing the nitinol fixation assembly 14. As a result of superior segmental correction from the interbody stabilization device 12 with increased cortical bone on the apophyseal ring contact with interbody endplates, inferior pedicle-based intradiscal fixation devices 14 may be deployed medially to the lateral legs 20, 22 of interbody plan. The super elasticity of nitinol allows for the material to be drawn into the straight deployment tube 324 from its curved state. The instrument 320 is able to load the nitinol into the straight deployment tube 324 by drawing it in from the threaded proximal end 48. The deployment tube 324 is customized for specific size offerings as the bend diameter, or cephalad-caudal height, of the nitinol rod 40 has a proportional rod thickness to improve super elastic properties in proportion to its strength.

Before shifting the end-effector 90 onto the planned trajectory for fixation deployment, navigation may prompt the surgeon to re-register with a sagittal and coronal c-arm shot to account for the segmental correction and a shift of inferior and superior vertebrae 2 from interbody expansion. Once re-registered, the pre-op plan for nitinol fixation 14 may be confirmed and/or altered to fit revised patient anatomy. Once the plan is set, the end-effector 90 moves into position and a powered pedicle prep drill may be used to drill a hole to the planned depth of the deployment instrumentation 320 into the inferior pedicle 8. The nitinol deployment instrument 320 is subsequently sent down the end-effector 90 and locked into the axial locking cap 130 after the guide bar assembly 102 has been removed.

The nitinol rod 40 may be set into the prepped hole, locked into the end-effector 90, and is ready for impaction for deployment. The properties of super elastic nitinol allow for the nitinol to return to its natural, curved state throughout the deployment process, sweeping from the inferior pedicle 8, thru the intradiscal space 4, medially to the lateral interbody legs 20, 22, and into the superior vertebral body 6. After the impaction cap 336 bottoms-out and the rod 40 is fully deployed, the instrumentation 320 may be removed. The pedicle screw 42 may be inserted and driven over the proximal threads 48 of the nitinol rod 40 to purchase the existing cortical bone in the pedicle 8 and anchor the proximal end 44 of the nitinol rod 40 to the inferior pedicle 8. Additional features may be used to lock the screw 42 to the nitinol rod 40, such as a snap ring in the pedicle screw 42 to snap into an external groove of the nitinol rod 40. The process of installing the second nitinol fixation assembly 14 may be repeated for the contralateral side.

The eighth step in the workflow may include final verification. After fixation 14 is deployed and assembled, a final verification may be used to ensure the final construct accomplished the pre-op plan targeted positions, and achieved segmental correction in the sagittal and coronal planes. The completed construct provides superior stabilization from a posterior approach and the fixation devices 14 do not violate the superior facet joint, thereby limiting adjacent segment disease.

The robotically-enabled procedure utilizes imaging, navigation, and robotics to enhance the quality and efficiency of the posterior procedure through planning and navigable instrumentation. The overall procedure may reduce radiation exposure compared to traditional surgeries. The bi-portal assembly and discectomy instruments provide for safe and repeatable direct decompression within the access window of the tubular approach. The discectomy instrumentation may increase the percent volume of soft tissue removed to increase volumetric area for interbody placement and bone graft. Segmental correction from the interbody stabilization device with independently controlled sagittal and coronal correction may provide for increased stability from increased endplate contact along the apophyseal ring. The posterior, MIS nitinol fixation implants avoid violation of superior facet joint and the potential iatrogenic effects bilateral pedicle constructs can cause.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A method for stabilizing the spine comprising:
   positioning an expandable interbody implant in a disc space between superior and inferior vertebrae, the expandable interbody implant having three articulating and expandable legs;
   deploying a first bendable rod from an ipsilateral pedicle of the inferior vertebra, thru the disc space, and into a vertebral body of the superior vertebra;
   inserting a first pedicle screw through the ipsilateral pedicle of the inferior vertebra and driving the first pedicle screw over the first bendable rod to anchor the first bendable rod;
   deploying a second bendable rod from a contralateral pedicle of the inferior pedicle, thru the disc space, and into the vertebral body of the superior vertebra; and
   inserting a second pedicle screw through the contralateral pedicle of the inferior pedicle and driving the second pedicle screw over the second bendable rod to anchor the second bendable rod,
   wherein the expandable interbody implant is positioned in the disc space by inserting a magnetic cable assembly attached to the expandable interbody implant through an ipsilateral cannula, inserting an articulating magnet retrieval tool through a contralateral cannula to magnetically attract and connect to the magnetic cable assembly, and retracting the articulating magnet retrieval tool back through the contralateral cannula, thereby pulling the cable assembly into the contralateral cannula and positioning the expandable interbody implant in the disc space.

2. The method of claim 1, wherein the three legs of the expandable interbody implant are articulated relative to one another to increase the overall footprint of the implant.

3. The method of claim 1, wherein the expandable interbody implant is placed along the apophyseal ring of the vertebrae for cortical bone support.

4. The method of claim 1, wherein the expandable interbody implant is expanded to independently control sagittal and coronal correction.

5. The method of claim 1, wherein the first intradiscal implant is deployed through an ipsilateral cannula and the second intradiscal implant is deployed through a contralateral cannula.

6. The method of claim 1, wherein the first and second intradiscal implants are positioned medially relative to the expandable interbody implant.

7. The method of claim 1, wherein the first and second bendable rods are each deployed with a deployment instrument having a deployment tube and a shaft with an impaction cap, wherein each bendable rod is deployed by striking the impaction cap, thereby forcing the rod to deploy out of the deployment tube.

8. A method of installing an expandable interbody implant in a disc space between two adjacent vertebrae comprising:
   inserting a cable assembly through an ipsilateral cannula, the cable assembly including a cable with a magnetic tip at one end and attachable to an expandable interbody implant at the other end, the expandable interbody implant having a first expandable lateral leg, a second expandable lateral leg, and a third central leg pivotably connected between the first and second lateral legs;
   inserting an articulating magnet retrieval tool through a contralateral cannula;
   articulating and guiding the articulating magnet retrieval tool toward the ipsilateral cannula to magnetically attract and connect to the magnetic tip of the cable assembly; and
   retracting the articulating magnet retrieval tool back through the contralateral cannula, thereby pulling the cable assembly into the contralateral cannula and positioning the expandable interbody implant in the disc space.

9. The method of claim 8 further comprising threading the cable assembly on the first expandable lateral leg of the expandable interbody implant before inserting the cable assembly through the ipsilateral cannula.

10. The method of claim 8 further comprising attaching a first inserter to the expandable interbody implant while placing the cable under tension.

11. The method of claim 10 further comprising feeding the expandable interbody implant through the ipsilateral cannula with the first inserter while the cable assembly pulls the expandable interbody implant into an articulated U-shaped position.

12. The method of claim 11, wherein after removing the cable assembly from the expandable interbody implant, attaching a second inserter to the expandable interbody implant such that the first and second inserters are rigidly connected to the first and second lateral legs, respectively, thereby providing for dual control of the expandable interbody implant.

13. The method of claim 12 further comprising inserting a driver through each of the first and second inserters to independently expand the first and second lateral legs to control sagittal and coronal correction.

\* \* \* \* \*